United States Patent
Sakai

(10) Patent No.: US 8,204,699 B2
(45) Date of Patent: Jun. 19, 2012

(54) ANALYZING APPARATUS, ANALYZING METHOD, AND COMPUTER-READABLE RECORDING MEDIUM STORING AN ANALYZING PROGRAM

(75) Inventor: Hidehisa Sakai, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 261 days.

(21) Appl. No.: 12/696,927

(22) Filed: Jan. 29, 2010

(65) Prior Publication Data
US 2010/0204932 A1 Aug. 12, 2010

(30) Foreign Application Priority Data
Feb. 12, 2009 (JP) ................................ 2009-030361

(51) Int. Cl.
*G01F 19/00* (2006.01)
*G01L 1/00* (2006.01)
(52) U.S. Cl. ............... 702/42; 702/33; 702/36; 702/43; 702/44; 702/150; 702/155
(58) Field of Classification Search ............... 702/33, 702/36, 42, 43, 44, 150, 155
See application file for complete search history.

(56) References Cited

U.S. PATENT DOCUMENTS
2002/0170360 A1 * 11/2002 Anand et al. .................. 73/849

FOREIGN PATENT DOCUMENTS
| JP | 62-003974 A | | 1/1987 |
| JP | 10-079408 A | | 3/1998 |
| JP | 2003-232709 A | | 8/2003 |
| JP | 2005-017054 | * | 1/2005 |
| JP | 2005-017054 A | | 1/2005 |

OTHER PUBLICATIONS

Rusmee, Pichai. "High Strength Composites," 2005.*

* cited by examiner

*Primary Examiner* — Sujoy Kundu
(74) *Attorney, Agent, or Firm* — Fujitsu Patent Center

(57) ABSTRACT

An analyzing method includes acquiring displacements with respect to loads applied of the test piece measured by the three-point bending test; calculating a first approximate expression of a relation of the displacements with respect to the loads applied in a first area where the relation is linear so as to determine an elasticity modulus of the test piece; extracting boundary value of a relation of strains caused by the displacements with respect to the loads so as to determine a yield stress value of the test piece; and calculating a second approximate expression of a relation of stress caused by the loads with respect to the strains caused by the displacements in a second area beyond the yield stress value on the basis of the yield stress value, the elasticity modulus, and the measurements in the second area.

9 Claims, 33 Drawing Sheets

FIG. 2

| LOAD (kgf) | DISPLACEMENT (mm) |
|---|---|
| −0.00061 | −0.00025 |
| −0.00058 | −0.00038 |
| −0.00063 | −0.0005 |
| 0.041401 | 0.24975 |
| 0.091394 | 0.499875 |
| 0.144203 | 0.749875 |
| 0.203997 | 0.999875 |
| 0.266155 | 1.25 |
| 0.32869 | 1.499875 |
| 0.392097 | 1.75 |
| 0.450547 | 2.000125 |
| 0.509161 | 2.250375 |
| 0.561693 | 2.500375 |
| 0.600011 | 2.75075 |
| 0.630337 | 3.00075 |
| 0.656213 | 3.251 |
| 0.680788 | 3.501125 |
| 0.695139 | 3.751375 |
| 0.719937 | 4.0015 |
| 0.742013 | 4.25175 |
| 0.787442 | 4.499626 |

LOAD-DISPLACEMENT MEASUREMENT DATA

Fig.7

| LOAD (kgf) | DISPLACEMENT (mm) |
|---|---|
| 0.018257 | −0.0005 |
| 0.060283 | 0.24975 |
| 0.110276 | 0.499875 |
| 0.163085 | 0.749875 |
| 0.22288 | 0.999875 |
| 0.285038 | 1.25 |
| 0.347573 | 1.499875 |
| 0.41098 | 1.75 |
| 0.469429 | 2.000125 |
| 0.528043 | 2.250375 |
| 0.580576 | 2.500375 |
| 0.618893 | 2.75075 |
| 0.64922 | 3.00075 |
| 0.675096 | 3.251 |
| 0.69967 | 3.501125 |
| 0.714021 | 3.751375 |
| 0.738819 | 4.0015 |
| 0.760896 | 4.25175 |
| 0.806325 | 4.499626 |

Fig.8

| i | Ai | Bi |
|---|----------|----------|
| 0 | 5.954648 | 5.954648 |
| 1 | 5.42414  | 5.689394 |
| 2 | 5.14938  | 5.509389 |
| 3 | 4.86427  | 5.34811  |

FIG. 9

| TEST PIECE LENGTH L (mm) | 20 |
|---|---|
| TEST PIECE WIDTH b (mm) | 10 |
| TEST PIECE THICKNESS h (mm) | 0.125 |

FIG. 11

| LOAD (kgf) | ACTUAL VALUE (mm) | THEORETICAL VALUE (mm) | ERROR β (%) | YIELD STRESS (kgf/mm²) |
|---|---|---|---|---|
| 0.581 | 2.500 | 2.447 | 2.141 | 74.325 |
| 0.619 | 2.751 | 2.559 | 6.963 | 79.347 |
| 0.649 | 3.001 | 2.645 | 11.849 | 83.491 |
| 0.675 | 3.251 | 2.717 | 16.437 | 87.198 |
| 0.700 | 3.501 | 2.783 | 20.516 | 90.832 |
| 0.714 | 3.751 | 2.821 | 24.806 | 93.309 |
| 0.739 | 4.002 | 2.885 | 27.896 | 97.087 |

Fig.12

| No. | α | n |
|---|---|---|
| 1 | 0.25 | 5 |
| 2 | 0.25 | 10 |
| 3 | 0.25 | 15 |
| 4 | 0.5 | 5 |
| 5 | 0.5 | 10 |
| 6 | 0.5 | 15 |
| 7 | 1 | 5 |
| 8 | 1 | 10 |
| 9 | 1 | 15 |

Fig.13

| | σ kgf/mm² | ε |
|---|---|---|
| Y | 74.325 | 0.005403 |
| 1.1Y | 81.7575 | 0.006494 |
| 1.2Y | 89.19 | 0.007875 |
| 1.3Y | 96.6225 | 0.009631 |
| 1.4Y | 104.055 | 0.011862 |
| 1.5Y | 111.4875 | 0.014688 |
| 1.6Y | 118.92 | 0.018245 |
| 1.7Y | 126.3525 | 0.022689 |
| 1.8Y | 133.785 | 0.028197 |
| 1.9Y | 141.2175 | 0.034967 |
| 2Y | 148.65 | 0.43221 |

FIG. 18

| LOAD F (kgf) | DISPLACEMENT ACCORDING TO FEM ANALYSIS (STRESS-STRAIN CURVE IGNORED) (mm) |
|---|---|
| 0.1 | 0.5337 |
| 0.2 | 0.9852 |
| 0.4 | 1.714 |
| 0.6 | 2.268 |
| 0.8 | 2.701 |

FIG. 20

| LOAD F (kgf) | DISPLACEMENT ACCORDING TO FEM ANALYSIS (STRESS-STRAIN CURVE: No.1) (mm) | ACTUAL VALUE (mm) | SQUARED RESIDUAL OF ERROR BETWEEN ACTUAL VALUE AND FEM ANALYSIS RESULT |
|---|---|---|---|
| 0.1 | 0.5337 | 0.498 | 0.001274 |
| 0.2 | 0.9852 | 0.95 | 0.001239 |
| 0.4 | 1.714 | 1.65 | 0.004096 |
| 0.6 | 2.268 | 2.6 | 0.1089 |
| 0.8 | 2.701 | 4.4 | 2.808976 |

FIG. 21

MANAGEMENT TABLE

| No. | α | n | RESIDUAL SUM OF SQUARES |
|---|---|---|---|
| 1 | 0.25 | 5 | 2.924486 |
| 2 | 0.25 | 10 | 2.911094 |
| 3 | 0.25 | 15 | 2.901071 |
| 4 | 0.5 | 5 | 2.90441 |
| 5 | 0.5 | 10 | 2.894399 |
| 6 | 0.5 | 15 | 2.887735 |
| 7 | 1 | 5 | 2.891066 |
| 8 | 1 | 10 | 2.884406 |
| 9 | 1 | 15 | 2.881079 |

ANALYZING APPARATUS, ANALYZING METHOD, AND COMPUTER-READABLE RECORDING MEDIUM STORING AN ANALYZING PROGRAM

CROSS-REFERENCE TO RELATED APPLICATION

This application is based upon and claims the benefit of priority of the prior Japanese Patent Application No. 2009-030361, filed on Feb. 12, 2009, the entire contents of which are incorporated herein by reference.

FIELD

The embodiments discussed herein are related to an analyzing apparatuses, analyzing methods, and computer-readable recording media storing analyzing programs intended for measurement of stress-strain relationships of test pieces.

BACKGROUND

Typically, structural materials of various electronic apparatuses including personal computers and mobile phones are designed under the assumption that such apparatuses may be used under stresses smaller than the yield stresses of the materials thereof. Therefore, the structures of such apparatuses can be designed if their linear material properties (moduli of longitudinal elasticity, i.e., Young's moduli) and linear material characteristics are known. With the reduced sizes and thicknesses of such apparatuses in recent years, however, there has been an increasing need to design apparatuses taking into consideration situations where the apparatuses may be subjected to stresses over the yield stresses of the materials thereof.

A characteristic of a material exhibited beyond a point at which a stress applied to the material exceeds the yield stress of the material and causes plastic deformation of the material is represented by a stress-strain characteristic. FIG. 31 shows an exemplary stress-strain curve of an aluminum alloy. As shown in FIG. 31, the stress and the strain are initially proportional to each other (where Hooke's law holds) as represented by a straight line passing the origin. When, however, the stress exceeds the yield stress, the stress-strain relationship becomes nonlinear as represented by a curve shown in FIG. 31. In the example shown in FIG. 31, the stress-strain relationship becomes nonlinear under a stress of about 350 MPa. The material characteristic representing a stress-strain relationship exhibited after the linear portion is the stress-strain property, which is a material value intrinsic to each individual material.

In a typical method of measuring a stress-strain curve of, for example, a metal material, a tensile test piece conforming to JIS Z 2201 (test pieces for tensile test for metallic materials) is prepared in accordance with JIS Z 2241 (method of tensile test for metallic materials), and the stress-strain curve is measured by performing a tensile test (see Japanese Laid-open Patent Publication No. 2003-232709). In this testing method, the initial gauge length L (mm) at the time of the preparation of the test piece under no load is defined first. Subsequently, the test piece is subjected to a load P (N), which is sequentially changed. At every change in the load P (N), the load P (N) and a gauge length L' (mm) corresponding thereto are measured, whereby a nominal strain $\epsilon$ is calculated in accordance with Equation (1):

A stress $\sigma$ is calculated from the initial cross section A of the test piece expressed by A=w (width)×t (thickness) and each of the loads P in accordance with Equation (2):

The test piece specified in JIS Z 2201, however, is very large. FIG. 32 shows a typical example of No. 1 test piece. Therefore, measurement of materials used for electronic apparatuses, such as rare metals including gold and gold compounds, expensive resin materials, and the like, costs an impractically large amount of money. In cases of thin-film materials that can only be provided with very small thicknesses, it is difficult to produce a test piece. Brittle materials such as bismuth-based metal compounds and some resin materials undergo substantially no elongation in tensile tests, resulting in difficulties in performing tensile tests with high accuracy.

For the material characteristic represented by the linear portion of the stress-strain curve, an elastic modulus, as a bend elastic modulus, is calculated by performing a bending test, specifically, a three-point bending test, described below. FIG. 33 is a diagram for describing the three-point bending test. In the three-point bending test, a characteristic is utilized that a deflection $\delta$ occurring when a concentrated load P is applied to a double-end-supported beam is inversely proportional to the elastic modulus and is proportional to the load. The deflection $\delta$ is calculated in accordance with Equation (3):

The elastic modulus may be calculated from the deflection $\delta$ and the load P in accordance with Equation (4) obtained by solving Equation (3) for the elastic modulus E:

In Equations (3) and (4), "I" denotes the second moment of area of the test piece and is expressed by "I=bh3/12", where b denotes the width of the test piece, and h denotes the thickness of the test piece. For example, JIS H 7406 specifies a test method for flexural properties of fiber reinforced metals.

In the bending test, since the load and the amount of deformation can be controlled more easily than in the tensile test, the elastic modulus can be measured more easily than in the tensile test. Particularly, when test pieces of substantially the same size are used in the two tests, the amount of deformation occurring in the bending test is larger than that occurring in the tensile test. Therefore, in the bending test, accurate measurement of elastic modulus can be easily performed even with a measurement apparatus having low accuracy in deformation measurement.

For example, a case of an aluminum test piece having an elastic modulus of about 70000 MPa and a rectangular shape with a thickness of 1 mm, a width of 10 mm, and a length of 100 mm will be considered. The load to produce an elongation of 1 mm in a tensile test is 7000 N (about 700 kgf) according to the following equation:

Whereas, the load to produce a displacement (deflection) of 1 mm in a bending test using the same test piece as the aforementioned one is 2.8 N (280 gf), which is calculated in accordance with Equation (6) below obtained from Equation (4) above:

Thus, it is obvious that the bending test is advantageous in measurement accuracy and load application cost (see Japanese Laid-open Patent Publication No. 2003-232709).

The stress-strain characteristic of a material beyond the point of yield stress, however, cannot be obtained from the displacement-load curve obtained in a three-point bending test.

In the bending test, a large displacement can be produced with a very small load. Moreover, bending deformation of a test piece made of very thin film, which is not suitable for the tensile test, can also be calculated, enabling such a test piece to undergo a material property test. On the other hand, in the tensile test, as described above, the stress-strain relationship can be directly calculated by applying a specific stress ($\sigma=P/A$) to a material and calculating the strain $\epsilon=\delta/L$ from the material elongation $\delta=L'-L$. The bending test has a problem in that the stress-strain relationship cannot be calculated directly from the relationship between the bending displacement $\delta$ and the load P. This is because the stress-strain relationship is nonlinear, making it difficult to estimate the original stress-strain relationship from the displacement-load relationship.

When the stress-strain relationship is linear, Hooke's law of $\sigma=E\epsilon$ holds in the stress-strain relationship. In addition, the stress and the external load are proportional to each other with a relationship $\sigma=kP$ ($\sigma=P/A$ for the tensile test, and $\sigma=M/Z=PL/(4Z)=3PL/(2bh2)$ for the bending test).

The strain and the displacement are also proportional to each other as expressed by $\epsilon=k\delta$ ($\epsilon=\delta/L$ for the tensile test, and $\epsilon=6\delta h/L2$ for the bending test). Therefore, the stress and the strain can be estimated from the displacement $\delta$ and the load P, which are measurable with ease.

Even if the stress-strain relationship is nonlinear, the stress can be estimated from the load as long as there is a proportional relationship expressed by $\sigma=kP$ between the stress and the load. However, the load and the stress beyond the point of yield of the material are not proportional to each other, and the relationship there between changes nonlinearly, following the stress-strain curve of the material. Specifically, the relationship $\int \sigma \cdot y \cdot dA = \int \sigma(y) \cdot y2 \cdot dy = M = PL$ holds.

When a stress over the yield stress acts on a test piece, the internal stress occurring in the test piece changes nonlinearly, following the stress-strain curve, in accordance with a length y in the thickness direction from the neutral axis of the test piece (if the test piece is made of a homogeneous material having a rectangular cross section, the neutral axis lies in the center in the thickness direction). Consequently, the relationship between the maximum stress $\sigma$ and the external load P also changes nonlinearly.

When the displacement $\delta$ is not very large, the strain and the displacement are proportional to each other, the same as in the foregoing case; even if the stress exceeds the yield stress and the stress-strain relationship becomes nonlinear. Specifically, the strain in the bending test is expressed by $\epsilon=6\delta h/L2$.

Nevertheless, when the displacement is large, the strain-displacement relationship becomes nonlinear. Therefore, in a test in which the amount of deformation is large and the stress-strain relationship is nonlinear, various nonlinear relationships occur simultaneously, resulting in difficulties in estimating the original stress-strain relationship of the material from the displacement $\delta$ and the load P.

In contrast, if the nonlinear stress-strain relationship of a material is known and the shape of a test piece of the material and loading conditions are explicitly provided, it is possible to estimate the load-displacement relationship. For simplicity, a case where the strain-displacement relationship is linear will be described. First, a certain amount of displacement $\delta$ is defined, whereby the strain can be calculated from the relationship $\epsilon=6\delta h/L2$.

Subsequently, a stress $\sigma$ corresponding to the strain c is calculated from the stress-strain curve. Lastly, integration of the stress is performed in accordance with the relationship $\int \sigma(y) \cdot y2 \cdot dy = M = PL$, whereby a load P to produce the displacement $\delta$ is obtained. Thus, the relationship between $\delta$ and P can be calculated. Even if the displacement-stress relationship is nonlinear, the same procedure can be taken. First, a certain amount of displacement $\delta$ is defined, and the strain $\epsilon$ is obtained by iterative calculation. Subsequently, a stress $\sigma$ corresponding to the strain $\epsilon$ is calculated from the stress-strain relationship. Lastly, integration of the stress is performed in accordance with the relationship $\int \sigma(y) \cdot y2 \cdot dy = M = PL$, whereby a load P to produce the displacement $\delta$ is obtained.

As described above, if the stress-strain relationship is known, it is possible to calculate the load-displacement relationship in the three-point bending test. In contrast, even if the load-displacement relationship is known, the stress-strain relationship cannot be calculated. Nevertheless, if a stress-strain relationship close to the genuine stress-strain relationship is reproduced from a few parameters in a certain manner, it is possible to estimate the stress-strain relationship from the load-displacement relationship.

SUMMARY

A measurement apparatus includes an elastic-modulus-calculating section configured to acquire a result of a three-point bending test performed on a test piece and to calculate an elastic modulus of the test piece in accordance with a gradient of a curve representing a load-displacement relationship included in the result of the test; a theoretical-value-determining section configured to calculate, in a case where ends of the test piece are supported, a theoretical value representing a relationship between a load to be applied to the test piece and a displacement corresponding thereto for each of different friction coefficients and to determine which of the calculated theoretical values produces the smallest error with respect to the result of the test; a yield-stress-calculating section configured to determine, in accordance with the theoretical value determined by the theoretical-value-determining section and the result of the test, a load under which the error between the theoretical value and the result of the test is larger than or equal to a specified value as a yield start load and to calculate a yield stress of the test piece in accordance with the determined yield start load; and a stress-strain-relationship-calculating section configured to calculate a stress-strain relationship of the test piece in accordance with the elastic modulus and the yield stress.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

FIG. 2 shows an exemplary structure of load-displacement measurement data;

FIG. 7 shows an exemplary structure of post-adjustment data;

FIG. 8 shows gradients obtained from the post-adjustment data shown in FIG. 7;

FIG. 9 shows exemplary dimensions of a test piece;

FIG. 11 shows the results of yield-stress calculations;

FIG. 12 shows combinations of parameter levels;

FIG. 13 shows a relationship between σ and ε corresponding to case No. 1 shown in FIG. 12;

FIG. 18 shows a load-displacement relationship according to the FEM analysis results;

FIG. 20 shows a load-displacement relationship according to the FEM analysis results corresponding to case No. 1;

FIG. 21 shows an exemplary data structure of a management table;

DESCRIPTION OF THE EMBODIMENTS

[First Embodiment]

Figure 1:
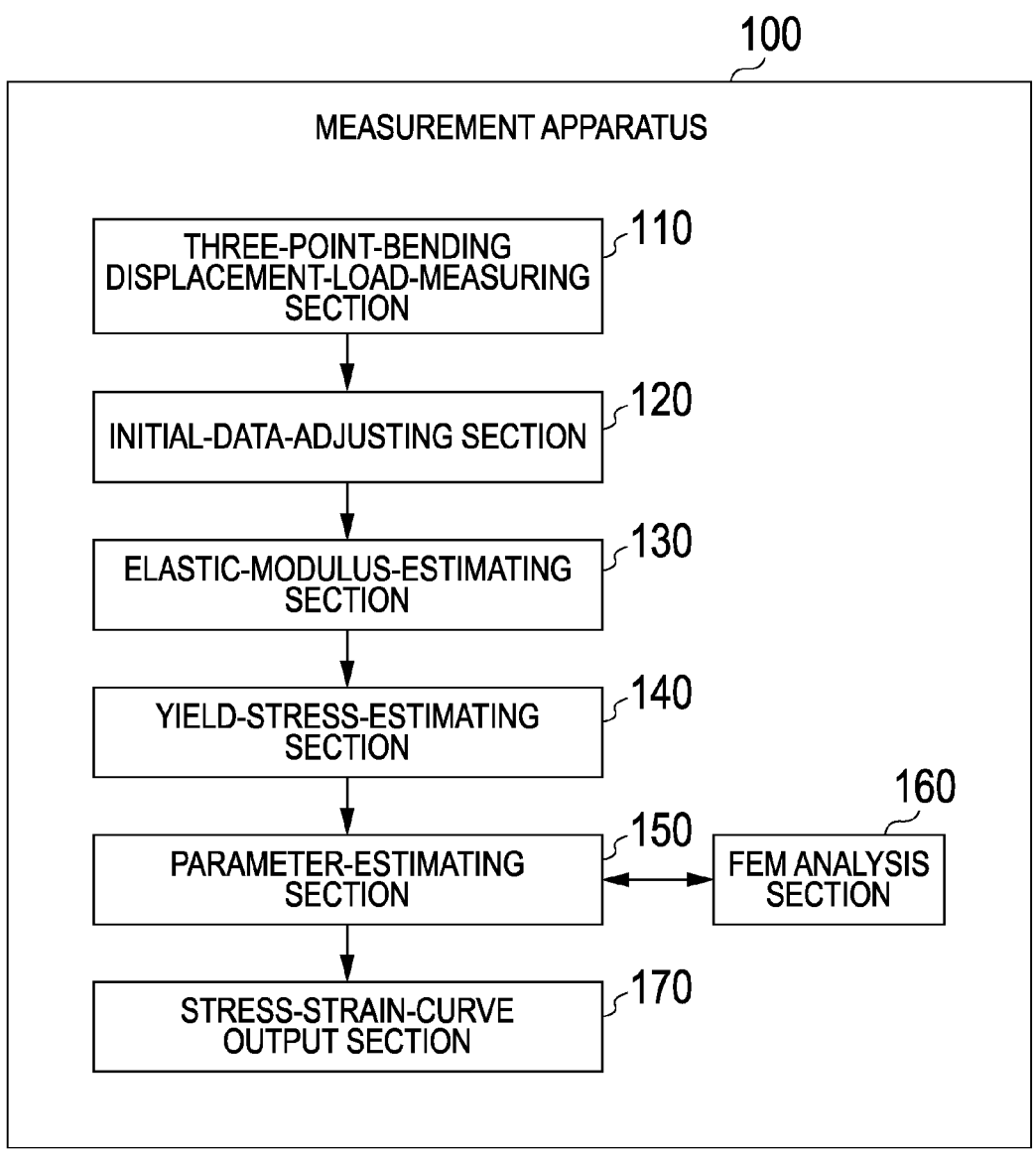
FIG. 1 is a functional block diagram of a measurement apparatus according to a first embodiment.

The configuration of a measurement apparatus according to an embodiment 1 will be described. FIG. 1 is a functional block diagram of the measurement apparatus according to the first embodiment. As shown in FIG. 1, a measurement apparatus 100 includes a three-point-bending displacement-load-measuring section 110, an initial-data-adjusting section 120, an elastic-modulus-estimating section 130, a yield-stress-estimating section 140, a parameter-estimating section 150, a finite-element-method (FEM) analysis section 160, and a stress-strain-curve output section 170.

Figure 3:
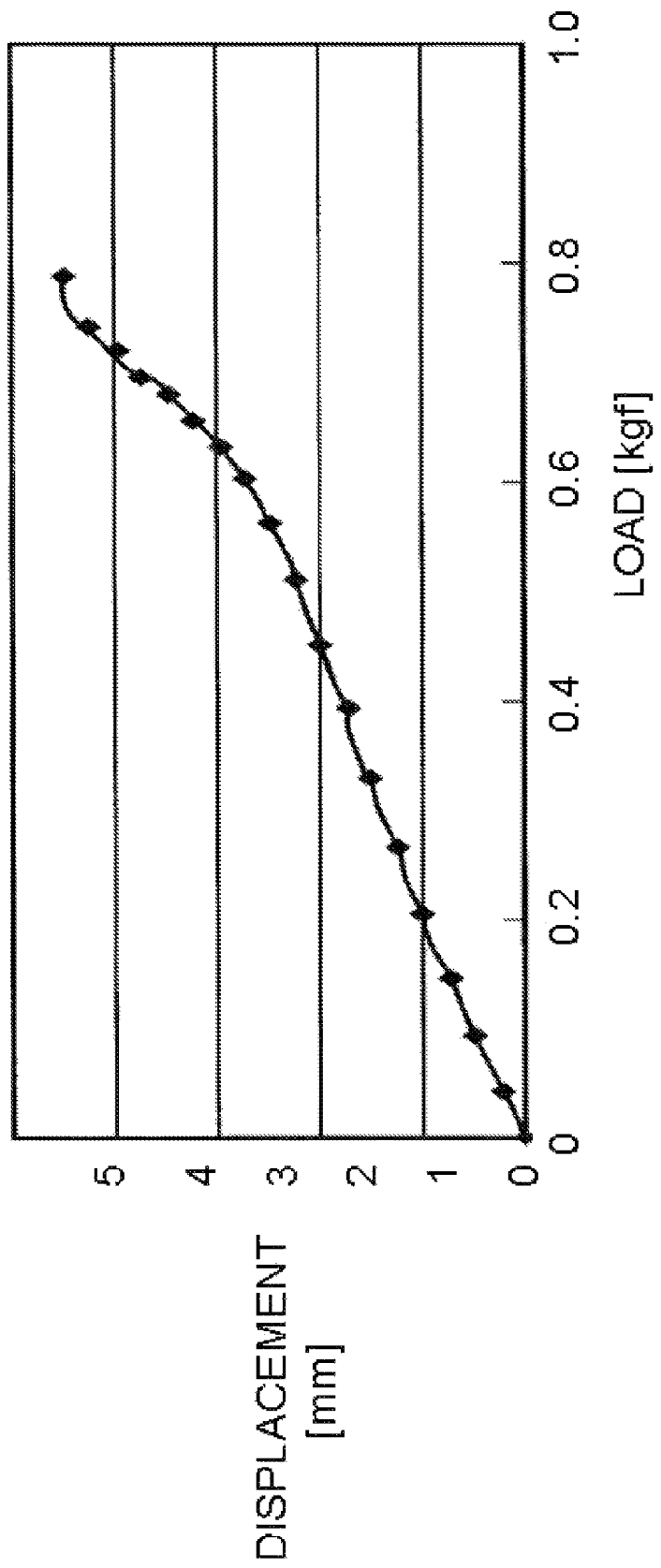
FIG. 3 shows a load-displacement curve corresponding to the load-displacement measurement data shown in FIG. 2.
Figure 33:
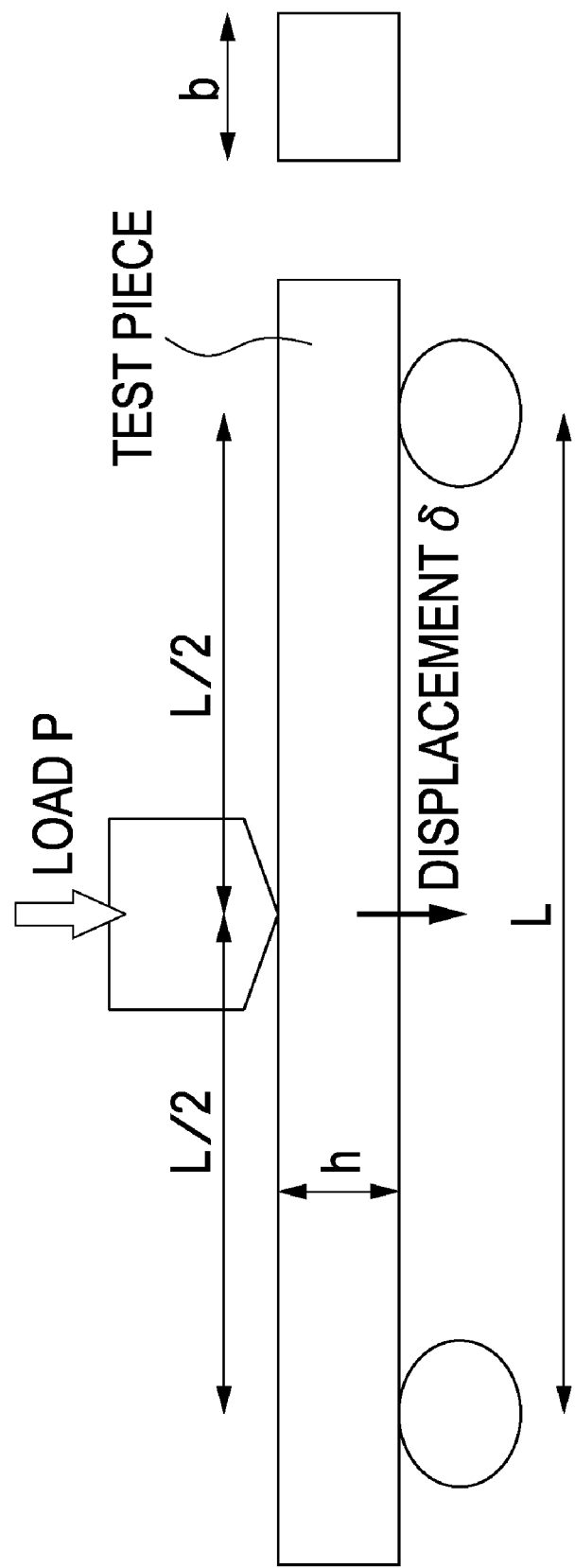
FIG. 33 is a diagram for describing a three-point bending test.

The three-point-bending displacement-load-measuring section 110 is a processing section that controls a three-point-bending test device, such as the one shown in FIG. 33, to initiate a three-point bending test, thereby acquiring load-displacement measurement data representing a load-displacement relationship. FIG. 2 shows an exemplary structure of the load-displacement measurement data. FIG. 3 shows a load-displacement curve corresponding to the load-displacement measurement data shown in FIG. 2. The three-point-bending displacement-load-measuring section 110 outputs the load-displacement measurement data to the initial-data-adjusting section 120.

Alternatively, a user may perform a three-point bending test and input the results of the test into the measurement apparatus 100. In that case, the three-point-bending displacement-load-measuring section 110 acquires the test results from the user through an input device (not shown) and outputs the acquired test results as load-displacement measurement data to the initial-data-adjusting section 120.

Figure 4:
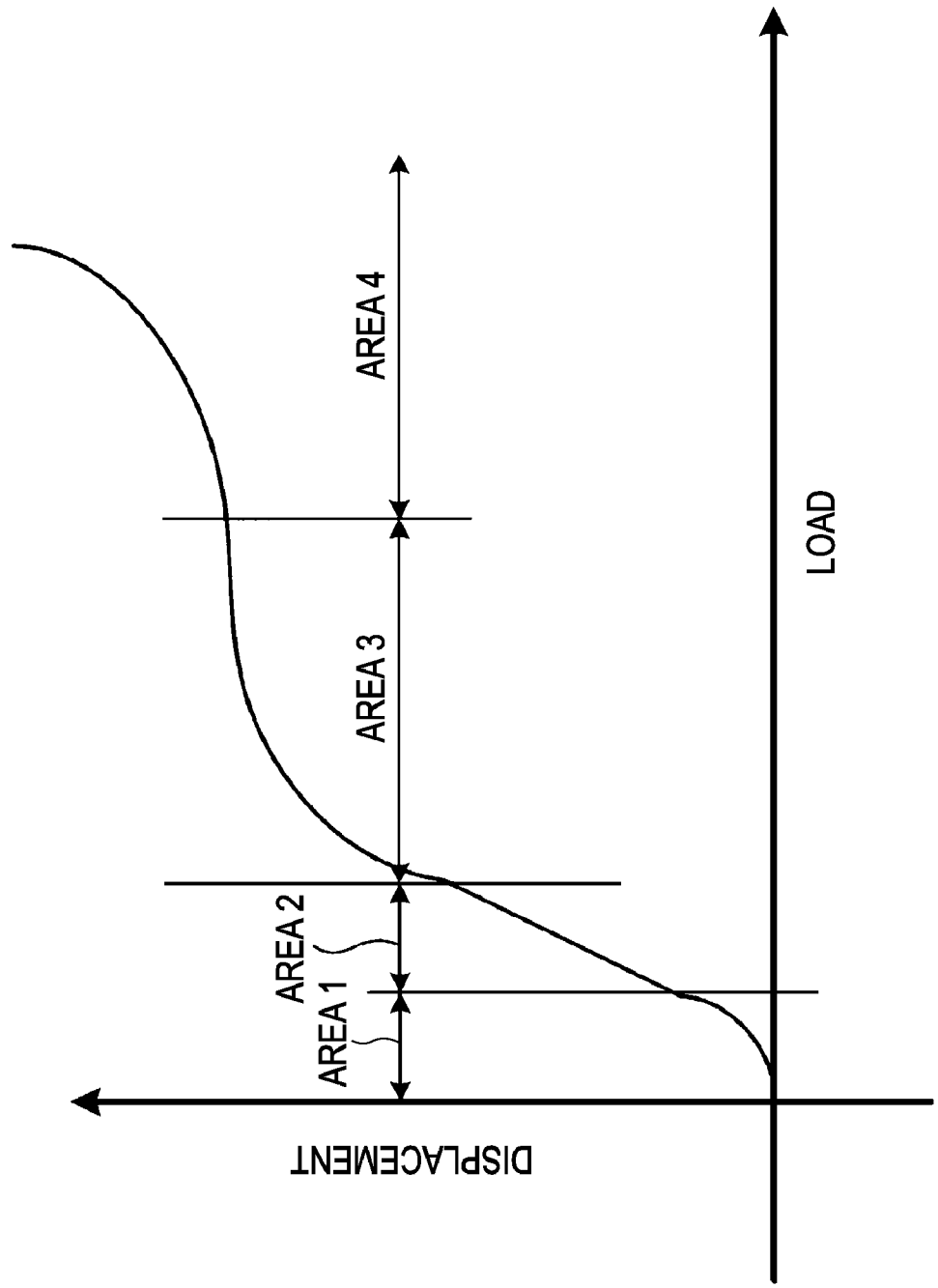
FIG. 4 schematically shows a load-displacement curve.

FIG. 4 schematically shows a load-displacement curve. When a load-displacement relationship is measured in a three-point bending test or the like, the measured curve is composed of several areas. The curve shown in FIG. 4 is composed of areas 1 to 4.

Area 1 is the initial area in which the load is very small, and the load-displacement relationship is occasionally not linear, represented by a nonlinear curve. This is because, for example, the backlash of the measurement apparatus and the contact area between a pressing jig and the test piece gradually change with an increasing pressing force, and the amount of displacement and the pressing force are therefore not proportional to each other at the beginning.

In area 2, the load-displacement relationship is linear, that is, the stress and the strain are proportional to each other in accordance with Hooke's law. In area 2, the elastic modulus can be calculated from the load-displacement relationship.

In area 3, both the load and the displacement are large, and there is a substantial effect of geometric nonlinearity. In some cases, the rigidity may appear to be high. This is because even if the stress-strain relationship is linear, the strain-displacement relationship or the load-displacement relationship is nonlinear. Area 3 is referred to as a geometrically nonlinear area. In area 3, an elastic modulus calculated from the load-displacement relationship contains a large error.

In area 4, a large displacement occurs relative to the applied load. This is because the stress-strain relationship is nonlinear, producing a large displacement relative to the load in accordance with the stress-strain curve.

The combination of areas 1 to 4 varies with factors such as loading conditions, the shapes of the test piece and the pressing jig, and so forth. For example, a case where there is substantially no area 1, a case where no area 4 representing plasticity is observed, a case where the boundary between area 3 and area 4 is unclear, a case where there is no area 3, that is, area 2 is directly followed by area 4, and a case where there is substantially no area 2, that is, area 1 is directly followed by area 3.

Referring back to FIG. 1, when the initial-data-adjusting section 120 acquires load-displacement measurement data, the initial-data-adjusting section 120 removes area 1 included in the load-displacement measurement data. That is, the initial-data-adjusting section 120 is a processing section that removes data corresponding to area 1 of load-displacement measurement data. The initial-data-adjusting section 120 outputs the load-displacement measurement data remaining after the removal of area 1 to the elastic-modulus-estimating section 130. Hereinafter, the load-displacement measurement data remaining after the removal of area 1 is referred to as post-adjustment data.

The processing operation performed by the initial-data-adjusting section 120 will be described. Specifically, first and second processing operations of removing area 1 will be described in that order. The initial-data-adjusting section 120 may remove area 1 by performing either the first or second processing operation.

The first processing operation of removing area 1 will be described. In the first processing operation, the initial-data-adjusting section 120 performs straight-line approximation of the load-displacement measurement data (load-displacement curve), finds points of intersection of the approximate straight line and the original curve, and removes a portion of the data prior to a first point of intersection.

Figure 5:
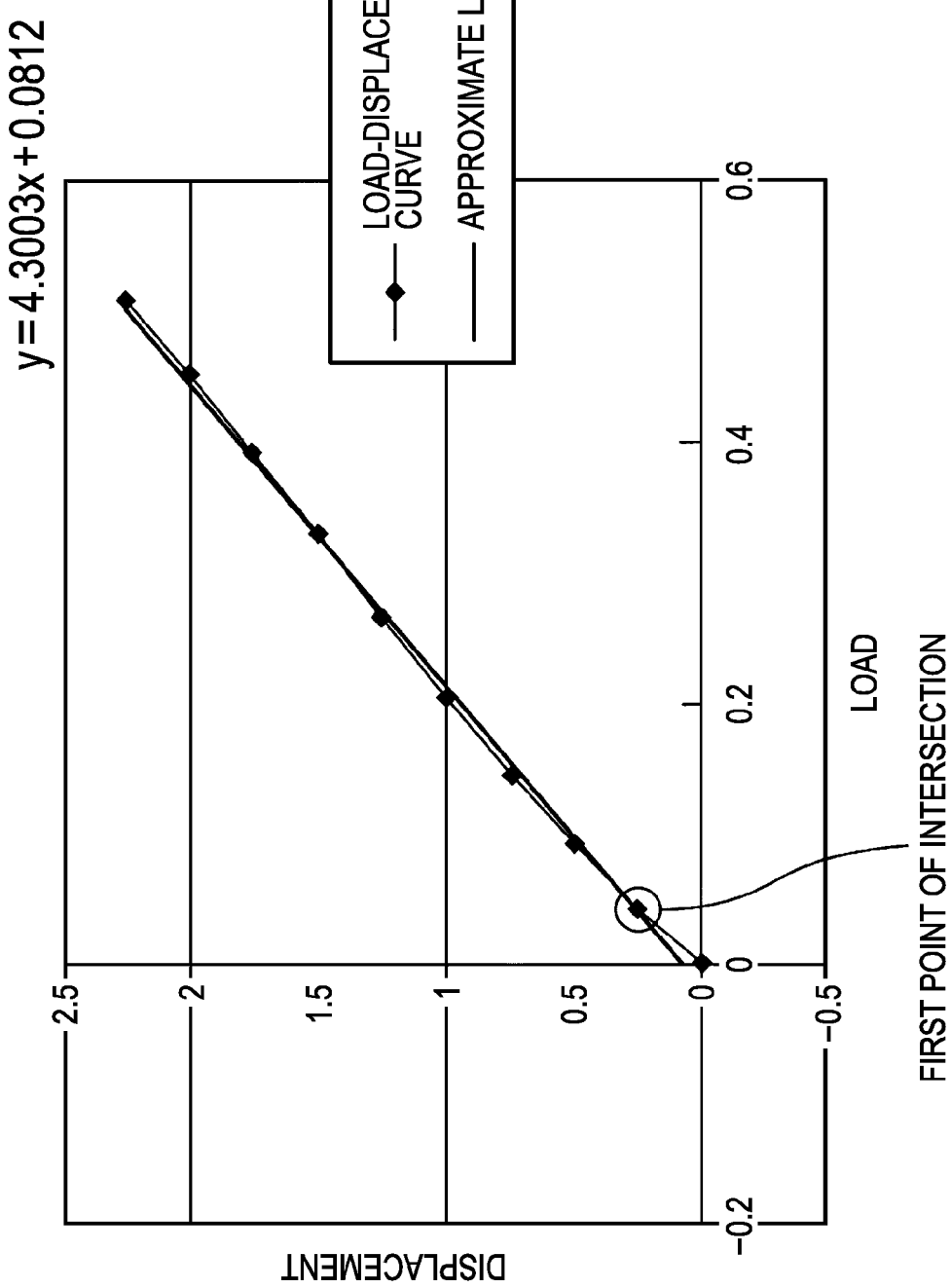
FIG. 5 is a diagram for describing a processing operation performed by an initial-data-adjusting section.

FIG. 5 is a diagram for describing the processing operation performed by the initial-data-adjusting section 120. Specifically, the initial-data-adjusting section 120 performs approximation of the load-displacement curve so as to obtain an approximate straight line, and finds points of intersection of the load-displacement curve and the approximate straight line.

Subsequently, the initial-data-adjusting section 120 defines one of the points of intersections at which the load is the smallest as the first point of intersection, and removes a portion of the load-displacement measurement data prior to the first point of intersection. Hereinafter, the load-displacement measurement data remaining after the removal of a portion thereof prior to the first point of intersection is referred to as first post-removal data.

Subsequently, the initial-data-adjusting section 120 performs straight-line approximation of the first post-removal data, more specifically, straight-line approximation of first M points (M=10, for example) of the first post-removal data, and finds the point of intersection of the approximate straight line and the X-coordinate line (the axis representing the load).

Figure 6:
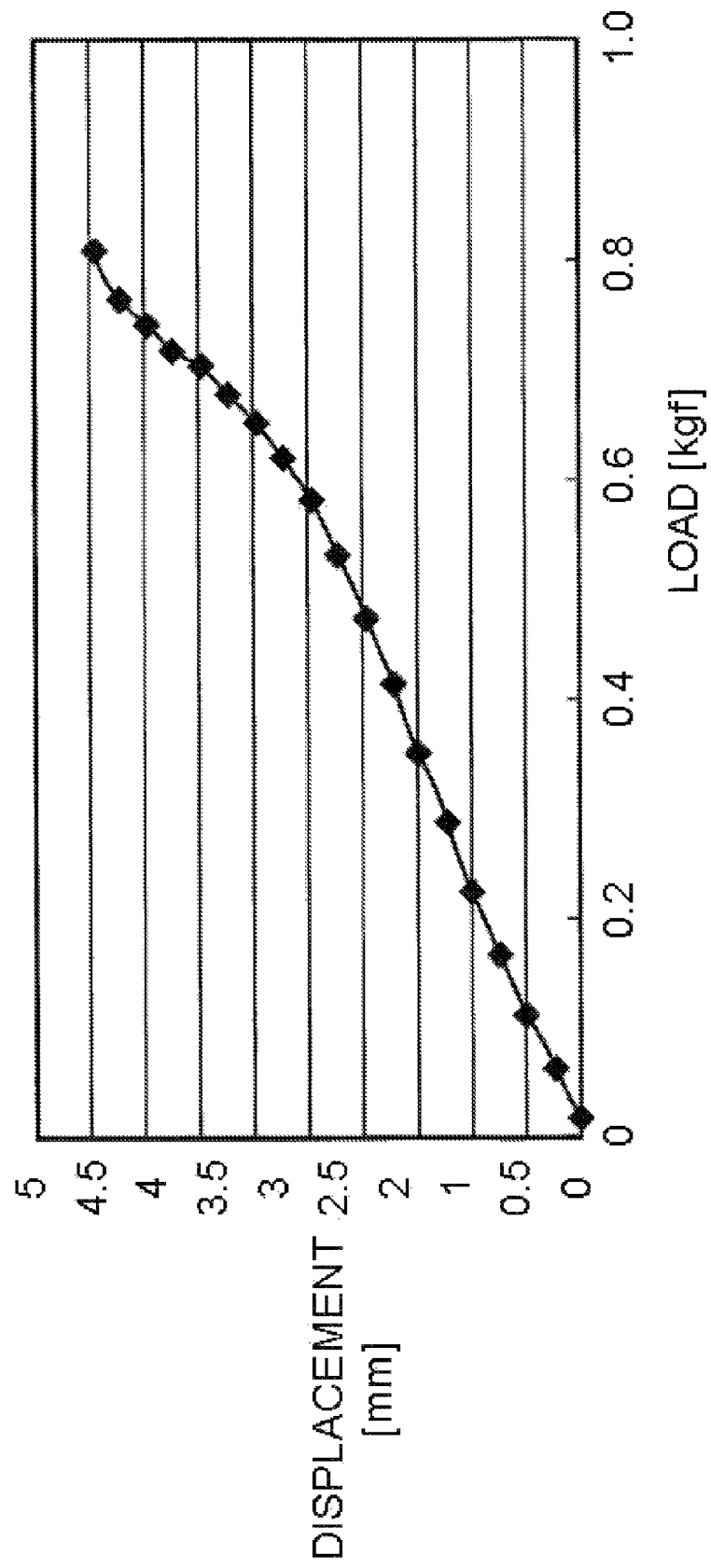
FIG. 6 is a diagram for describing the shifting of a curve performed by the initial-data-adjusting section.

Subsequently, the initial-data-adjusting section 120 shifts the curve representing the first post-removal data such that the coordinates of the found point of intersection becomes the X-coordinate origin. FIG. 6 is a diagram for describing the shifting of the curve performed by the initial-data-adjusting section 120. As shown in FIG. 6, the initial value of the curve representing the first post-removal data is shifted to the foregoing point of intersection. The initial-data-adjusting section 120 outputs the data on the shifted curve as post-adjustment data to the elastic-modulus-estimating section 130. FIG. 7 shows an exemplary structure of the post-adjustment data.

Next, the second processing operation of removing area 1 will be described. In the second processing operation, the initial-data-adjusting section 120 divides the load-displacement measurement data into several numbers L of areas and removes data in the initial area, thereby generating post-adjustment data.

Specifically, the initial-data-adjusting section 120 divides the load-displacement measurement data (load-displacement curve) into several areas (for example, 10 areas) and removes the initial area (the area in which the load and the displacement are the smallest) among the divided areas. Hereinafter, the load-displacement measurement data remaining after the removal of the initial area is referred to as second post-removal data.

Subsequently, the initial-data-adjusting section 120 performs straight-line approximation of the second post-removal data, more specifically, straight-line approximation of first M points (M=10, for example) of the second post-removal data, and finds the point of intersection of the approximate straight line and the X-coordinate line (the axis representing the load).

Subsequently, the initial-data-adjusting section 120 shifts the curve representing the second post-removal data such that the coordinates of the found point of intersection becomes the X-coordinate origin. The initial-data-adjusting section 120 outputs the data on the shifted curve as post-adjustment data to the elastic-modulus-estimating section 130.

The elastic-modulus-estimating section 130 is a processing section that estimates, at the acquisition of post-adjustment data, the elastic modulus in accordance with the gradient of a linear portion of the curve representing the acquired post-adjustment data. The processing operation performed by the elastic-modulus-estimating section 130 will be described specifically.

The elastic-modulus-estimating section 130 first calculates a gradient $A0$ of a line connecting initial data (data in the first row in FIG. 7) and two-point data (data in the second row in FIG. 7) subsequent thereto. Subsequently, the elastic-modulus-estimating section 130 calculates an approximate straight line with respect to three points including the initial data, the two-point data, and three-point data (data in the third row in FIG. 7) by a least squares method, and calculates a gradient $A1$ of the calculated approximate straight line.

Subsequently, the elastic-modulus-estimating section 130 calculates an approximate straight line with respect to four points including the initial data, the two-point data, the three-point data, and four-point data (data in the fourth row in FIG. 7) by a least squares method, and calculates a gradient $A2$ of the calculated approximate straight line. Likewise, a gradient $Ak$ (where k is a natural number) is calculated from the initial to k-point data. The elastic-modulus-estimating section 130 estimates the elastic modulus from the data of $A0$ to $Ak$.

The elastic-modulus-estimating section 130 calculates the average of $A0$ to $Ak$, as expressed in Equation (7) below, at every increase in k and defines the result of each calculation as $Bk$:

$$Bk=(A0+A1+\ldots+Ak)/k \qquad (7)$$

The elastic-modulus-estimating section 130 compares $Ak$ with $Bk$ at every increase in k. If the relationship $Ak>Bk$ holds for p successive times (for example p=3), the calculation of $Ak$ and $Bk$ is stopped, and the gradient $A$ of the straight line is fixed to $Bk-p$.

From the calculated gradient $A$ of elasticity, the elastic modulus is estimated in accordance with Equations (3) and (4) and is expressed by Equation (8):

$$E=L3/(48AI) \qquad (8)$$

In Equation (8), L denotes the supported length of the test piece, and I denotes the second moment of area (I=bh3/12) of the test piece. That is, the elastic-modulus-estimating section 130 calculates the elastic modulus in accordance with Equation (8), and outputs the calculated elastic modulus and the post-adjustment data to the yield-stress-estimating section 140. The elastic-modulus-estimating section 130 also acquires through the input device (not shown) information on the dimensions of the test piece, test-piece-fixing conditions, and so forth. If the genuine elastic modulus of the test piece is known, the known elastic modulus is taken, whereby the calculation of the elastic modulus can be omitted.

The processing operation in which the elastic-modulus-estimating section 130 calculates the elastic modulus from the post-adjustment data shown in FIG. 7 will be described specifically. FIG. 8 shows gradients obtained from the post-adjustment data shown in FIG. 7. The elastic-modulus-estimating section 130 first calculates a gradient $A0$ of a line connecting initial data (data in the first row in FIG. 7) and two-point data (data in the second row in FIG. 7) subsequent thereto. The result comes to 5.954648. In accordance with Equation (7), $B0$ is calculated to be 5.954648 (see the first row in FIG. 8). In the first row in FIG. 8, the relationship $A0=B0$ holds.

Subsequently, the elastic-modulus-estimating section 130 calculates an approximate straight line with respect to three points including the initial data, the two-point data, and three-point data (data in the third row in FIG. 7) by a least squares method. A gradient A1 of the approximate straight line is calculated to be 5.42414. In accordance with Equation (7), B1 is calculated to be 5.689394 (see the second row in FIG. 8). In the second row in FIG. 8, the relationship A1<B1 holds.

Subsequently, the elastic-modulus-estimating section 130 calculates an approximate straight line with respect to four points including the initial data, the two-point data, the three-point data, and four-point data (data in the fourth row in FIG. 7) by a least squares method. A gradient A2 of the approximate straight line is calculated to be 5.14938. In accordance with Equation (7), B2 is calculated to be 5.509389 (see the third row in FIG. 8). In the third row in FIG. 8, the relationship A2<B2 holds.

Subsequently, the elastic-modulus-estimating section 130 calculates an approximate straight line with respect to five points including the initial data, the two-point data, the three-point data, the four-point data, and five-point data (data in the fifth row in FIG. 7) by a least squares method. A gradient A3 of the approximate straight line is calculated to be 4.86427. In accordance with Equation (7), B3 is calculated to be 5.34811 (see the fourth row in FIG. 8). In the fourth row in FIG. 8, the relationship A3<B3 holds.

Upon the calculation of A3 and B3, the value of B has exceeded the value of A three consecutive times. Therefore, the value of A is fixed to the value of B0 (A is fixed to 5.954648). Subsequently, the elastic-modulus-estimating section 130 calculates the elastic modulus in accordance with Equation (8). FIG. 9 shows exemplary dimensions of the test piece. If the elastic modulus is calculated from the dimensions of the test piece shown in FIG. 9 and the value A=5.954648, the result comes to E=17196.6 kgf/mm2.

Referring back to FIG. 1, the yield-stress-estimating section 140 is a processing section that calculates, at the acquisition of an elastic modulus and post-adjustment data, the yield stress from the acquired elastic modulus and post-adjustment data. The yield-stress-estimating section 140 outputs the elastic modulus and the yield stress to the parameter-estimating section 150. The processing operation performed by the yield-stress-estimating section 140 will be described specifically. First, the yield-stress-estimating section 140 separates the effect of geometric nonlinearity from the elastic modulus obtained from the post-adjustment data.

A concentrated load F and a warpage u in a case where the effect of geometric nonlinearity in the three-point bending test is included are expressed by Equation (9) according to a large-deformation theory: where α is a constant determined in accordance with the condition of the axial-direction boundary, and l=L/2. Under a boundary condition that the X-direction displacements at two ends of the test piece are fixed to zero, Equation (9) can be approximately expressed as follows:

In Equation (10), if the warpage u is very small relative to the thickness h of the test piece, the second member on the right side can be ignored. Hence, the relationship between the concentrated load F and the warpage u is expressed as follows:

Equation (11) is substantially equal to the solution of a linear beam theory expressed by Equation (3).

In contrast, if the warpage u is large relative to the thickness h of the test piece, the first member on the right side of Equation (10) can be ignored. Hence, the relationship between the concentrated load F and the warpage u is expressed as follows:

The warpage u calculated in accordance with Equation (12) is as follows:

Equation (13) shows that the warpage u is proportional to the cubic root of the concentrated load F.

In a case where the two ends of the test piece are free or constrained under a specific load, the relationship between the load and the warpage u can be expressed by Equation (9) above. In the case where the two ends of the test piece are constrained under a specific load T, the displacement (warpage) is calculated by calculating the value of α in accordance with Equation (14) below and substituting the result into Equation (9):

In the case where the test piece has free ends, when the friction coefficient is denoted by μ, a load expressed by T=μF acts on the test piece. This equation is substituted into Equation (14), and the result of the substitution is further substituted into Equation (9), whereby the warpage u is calculated.

The friction coefficient μ depends on the surface conditions of the test piece and the support on which the test piece is placed, and it is difficult to determine a specific value of the friction coefficient μ before measurement. Therefore, in the first embodiment, the friction coefficient μ is estimated from the displacement-load curve (post-adjustment data) obtained from the result of the bending test. The estimation is performed as follows.

First, the yield-stress-estimating section 140 identifies an area of the displacement-load curve in which geometric nonlinearity is predominant. If there is no area in which geometric nonlinearity is predominant or if such an area cannot be identified, the first-half area of the data is identified as the foregoing area, as in the default setting.

The yield-stress-estimating section 140 calculates, with the initial friction coefficient μ being set to zero (μ=0), a theoretical displacement $u0i$ for each actually measured load Fi in accordance with Equations (9) and (14). The yield-stress-estimating section 140 calculates the difference sum of squares for each load Fi with respect to the corresponding actual displacement ui and theoretical displacement $u0i$, thereby calculating the error sum of squares Δ.

The yield-stress-estimating section 140 repeats the calculation of the error sum of squares Δ by adding the difference Δμ (Δμ=0.1, for example) to the friction coefficient μ until the friction coefficient μ reaches a specified value. The yield-stress-estimating section 140 compares the error sums of squares Δ calculated for the different friction coefficients μ with each other, and determines one of the friction coefficients μ that produces the smallest error sum of squares Δ as the genuine friction coefficient.

The load-displacement relationship in the post-adjustment data can be calculated in accordance with Equations (9) to (13), ignoring measurement errors. If there is any deviation between the displacement calculated in accordance with Equations (9) to (13) and the actual displacement, the difference is considered to be caused by the nonlinear stress-strain characteristic of the material. Ignoring the effect of measurement errors, if the actual displacement substantially agrees with the result of calculation performed in accordance with Equations (9) to (13), no effect of nonlinear stress-strain characteristic (plasticity) can be observed. Therefore, the stress-strain relationship in the area representing plasticity cannot be estimated.

Figure 10:
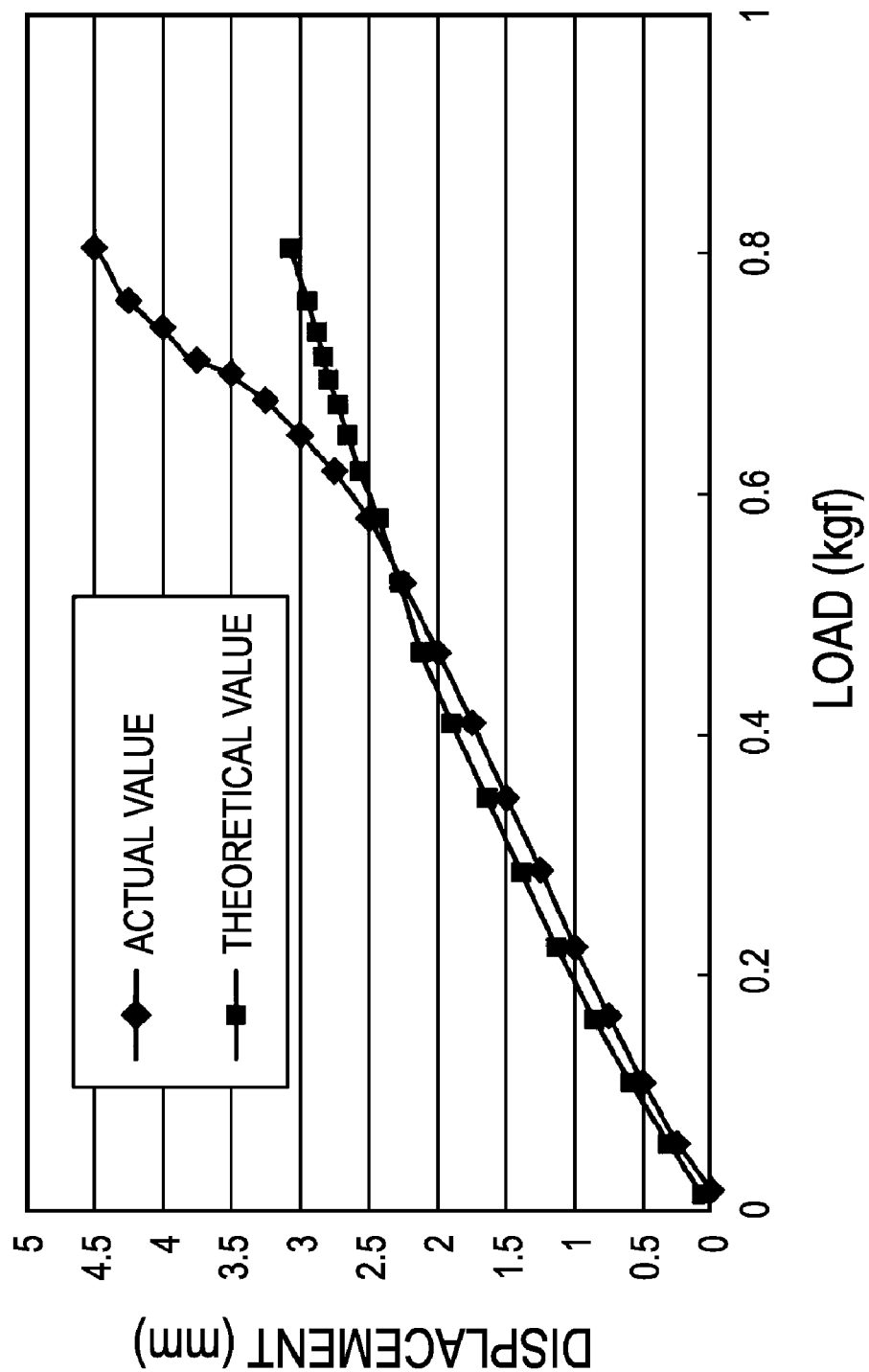
FIG. 10 shows actual and theoretical load and displacement.

A case will be described where the yield-stress-estimating section 140 calculates the theoretical warpage in accordance with Equations (9) and (14) taking geometric nonlinearity (large deformation) into consideration with an elastic modulus of E=17196.6 kgf/mm2. Since the test piece used in the measurement according to the embodiment 1 has free ends, an exemplary tension T at the ends is also calculated with a friction coefficient μ of 0.5. FIG. 10 shows actual and theoretical load and displacement. As shown in FIG. 10, the deviation between the theoretical and actual values becomes significant beyond a load of about 0.6 kgf. This means that the material starts to yield under the foregoing load, where the stress-strain effect is observed.

Next, calculation of the yield stress performed by the yield-stress-estimating section 140 will be described. The yield-stress-estimating section 140 calculates the yield stress from the post-adjustment data and the theoretical values of the load-displacement curve (see FIG. 10) obtained taking geometric nonlinearity into consideration.

If there is no nonlinear stress-strain effect, such as yield stress, in the test-piece material, the actual values agree with the theoretical values. The yield-stress-estimating section 140 finds the smallest one of the loads at each of which the error between the theoretical value and the actual value shown in FIG. 10 is larger than or equal to a predetermined value of β% (for example, 10%), and determines the smallest load as the yield-start load F*.

Supposing that the test-piece material is a perfect elasto-plastic body, the stress beyond the point of yield is constantly equal to the yield stress Y of the material. When the thickness of the test piece in the yielding area is h0, the following equation holds in accordance with the equilibrium of moment.

The maximum moment M in the three-point bending test is expressed as follows:

In addition, when the load F is equal to the yield-start load F*, Equations (15) and (16) are equal to each other. Furthermore, supposing that the yield-area thickness h0 and β% of h are equal to each other (h0=βh) when the load F is equal to the yield-start load F*, the yield stress Y is expressed as follows in accordance with Equations (15) and (16):

FIG. 11 shows the results of yield-stress calculations. As shown in FIG. 11, when the load is 0.581 kgf, the actual value (displacement) is 2.500 mm and the theoretical value (displacement) is 2.447 mm, with an error in the theoretical value being 2.141. If the load 0.581 kgf is defined as the yield-start load F*, the yield stress Y is calculated to be 74.325 kgf/mm2 in accordance with Equations (15) and (16).

Referring back to FIG. 1, the parameter-estimating section 150 is a processing section that estimates and identifies, at the acquisition of an elastic modulus E and a yield stress Y, parameters n and α included in the following equation by Ramberg-Osgood approximation:

By identifying the parameters n and α in Equation (18), the stress-strain relationship is calculated from the elastic modulus and the yield stress (the results of the three-point bending test). After identifying the parameters n and α, the parameter-estimating section 150 outputs information on the identified parameters n and α, the elastic modulus, and the yield stress to the stress-strain-curve output section 170.

The processing operation performed by the parameter-estimating section 150 will be described specifically. Exemplary equations expressing stress-strain relationships include Equation (18). Hereinafter, taking Equation (18) as an example, a method of determining parameters in a complex model equation will be described.

In Equation (18), n and α are unknown constants, which are the material values to be calculated. The elastic modulus E and the yield stress Y in Equation (18) are calculated by the elastic-modulus-estimating section 130 and the yield-stress-estimating section 140, respectively. It is difficult to identify the unknown parameters included in Equation (18) by a linear least-squares method because linear approximation cannot be performed easily by simply converting the parameters into variables.

Therefore, the embodiment 1 proposes a method of approximately estimating the parameters n and α by using an approximate polynomial. For an object (test piece) to be measured having unknown material values, one of materials similar thereto whose parameters are known is selected, and initial material values are estimated. The initial material values are defined as initial estimated values (α0 and n0).

The parameter-estimating section 150 sets several levels for each of the material parameters by positively and negatively changing the parameter by a certain number of percent (for example, 5% to 100%) with reference to the corresponding initial estimated value of the object to be measured. Specifically, for the parameter n, the initial estimated value n0 is set to 10, and the set value is changed by ±50%, whereby values of different levels, i.e., 5, 10, and 15, are set. Likewise, values of different levels of the parameter α are set with reference to the corresponding initial estimated value.

For example, three levels are set for each of the parameters (material values) n and α as follows:

Parameter n (level 1=n1, level 2=n2, and level 3=n3)
Parameter α (level 1=α1, level 2=α2, and level 3=α3)

The parameter-estimating section 150 makes combinations of levels of the parameters, and calculates the relationship between the strain ε and the stress σ for each of the combinations by substituting the parameters of individual levels defined in the combination, for example, material values of α3 and n3, into Equation (17). To estimate a stress-strain curve with a certain level of accuracy, the stress σ is set as follows. The upper limit of the yield stress Y is set to, for example, a value twice the calculated yield stress Y, and the range from Y to 2Y is divided into ten sub-ranges. Subsequently, the parameter-estimating section 150 calculates the value of εi for each value of σi (σ1=Y, . . . , and σ10=2Y) in accordance with Equation (18).

The ranges in which the parameters are changed are set empirically. If there are no empirical factors, all the parameters are changed by a uniform number of percent (for example, 50%) of the original material values. The parameter-estimating section 150 calculates a virtual stress-strain relationship (stress-strain curve) by substituting a combination of parameters of individual levels (for example, α2 and n3) into Equation (18).

The parameter-estimating section 150 outputs the virtual stress-strain relationship to the FEM analysis section 160, and acquires the displacement-load relationship from the FEM analysis section 160. In the first embodiment, there are two unknown parameters n and α and three levels are set for each of the parameters. Therefore, the parameter-estimating section 150 calculates nine cases of virtual stress-strain relationships using a round-robin algorithm, and stores displacement-load relationships corresponding to the respective cases.

The parameter-estimating section 150 compares actual displacements ui under respective loads Fi with displacements ui' in each of the cases calculated by finite element analysis, and calculating the errors between the displacements ui and the displacements ui' for each of the cases. Subsequently, the parameter-estimating section 150 calculates the error sum of squares under the loads Fi for each of the cases.

With reference to the parameter levels and the error sum of squares for each of the cases, the parameter-estimating section 150 expresses the squared error between the actual value and the calculated value in the form of an approximate expression using the parameters. The approximate expression is provided by a least-squares method or the like. The approximate expression may be provided as a polynomial expressed by material values, as provided below, or by any of other general functions (trigonometric function, logarithmic function, exponential function, and the like):

$$(\text{Error})2 = a1n2 + a2n + b1\alpha2 + b2\alpha + c1n\alpha + C \quad (19)$$

where a1, a2, b1, b2, c1, and C are constants determined by a least-squares method, and n and α denote material values.

In accordance with an error minimization principle in which the squared error expressed by Equation (19) is minimized, the parameter-estimating section 150 identifies the parameters n and α that minimize the error with respect to the actual value. The material values n and α that minimize the squared error may be determined either by an algorithm of general-purpose mathematical programming, such as sequential quadratic programming, or by an optimization algorithm, such as a genetic algorithm or an annealing method, similar thereto.

The following describes parameters α and n obtained when the elastic modulus E is 17196.6 kgf/mm2, the yield stress Y is 74.325 kgf/mm2, the initial value α0 of the parameter α is 0.5, the initial value n0 of the parameter n is 10, and the levels of the parameters α and n are α1=0.25, α2=0.5, α3=1, n1=5, n2=10, and n3=15.

FIG. 12 shows combinations of the foregoing parameter levels. As shown in FIG. 12, there are nine combinations of parameter levels. The parameter-estimating section 150 substitutes the values of α and n into Equation (18) sequentially from cases No. 1 to No. 9, thereby calculating the relationship between σ and ε for each of the cases.

FIG. 13 shows the relationship between G and c corresponding to case No. 1 shown in FIG. 12. The yield stress Y is calculated to be 74.325. The range from Y to 2Y is divided into ten sub-ranges, and values of εi corresponding to respective values of σi (σ1=Y, ..., and σ10=2Y) are calculated. The same as for case No. 1, the parameter-estimating section 150 calculates values of εi corresponding to respective values of εi for each of cases No. 2 to No. 9.

Figure 14:
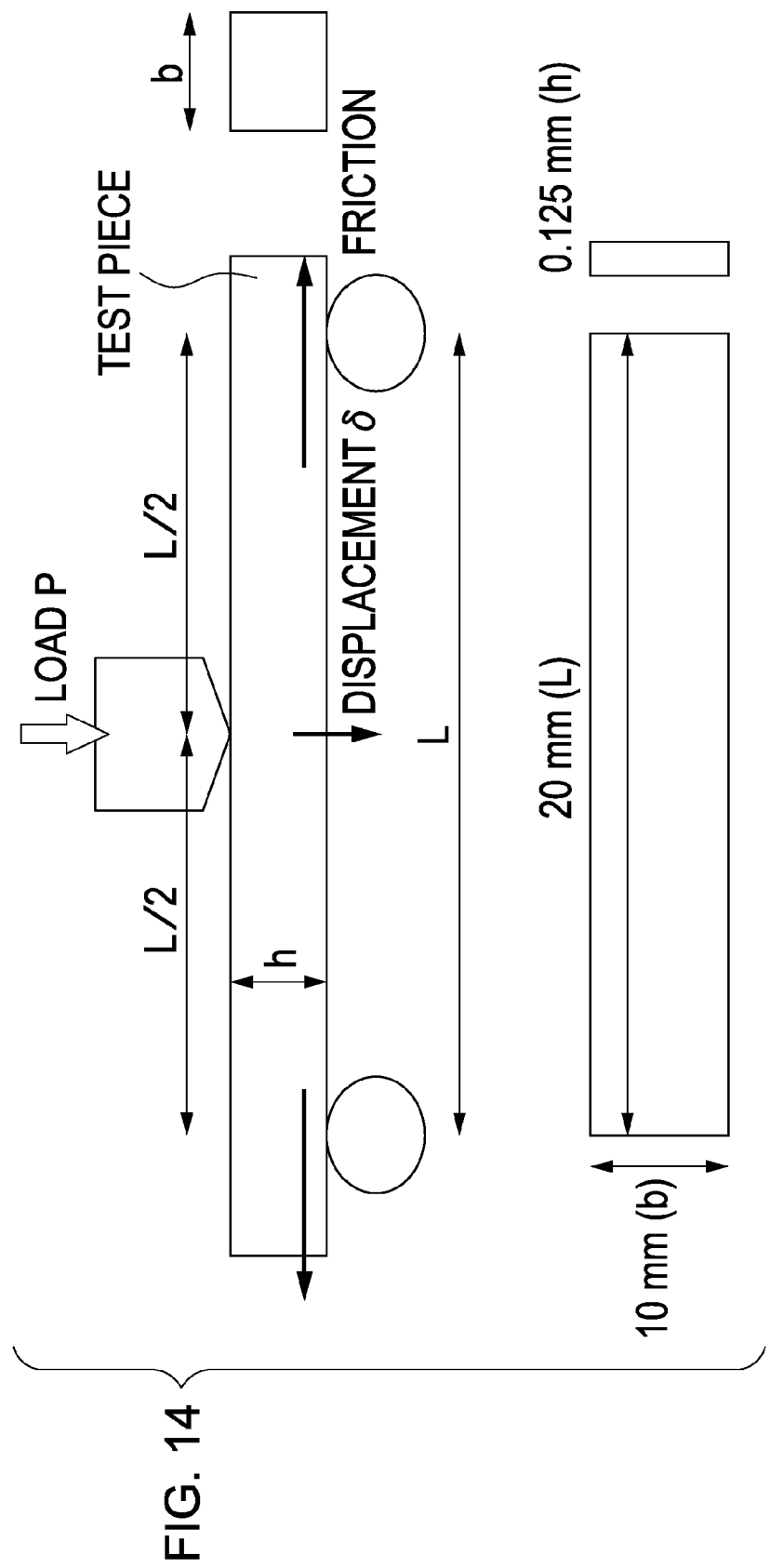
FIG. 14 shows specifications of a test piece.

The elastic modulus E is 17196.6 kgf/mm2. From the elastic modulus and the stress-strain curve corresponding to the values shown in FIG. 12, the warpage of the test piece under a specific load is calculated by a finite element method. FIG. 14 shows specifications, including dimensions, of the test piece. As shown in FIG. 14, the test piece has a length of 20 mm, a width of 10 mm, and a thickness of 0.125 mm.

Figure 15:
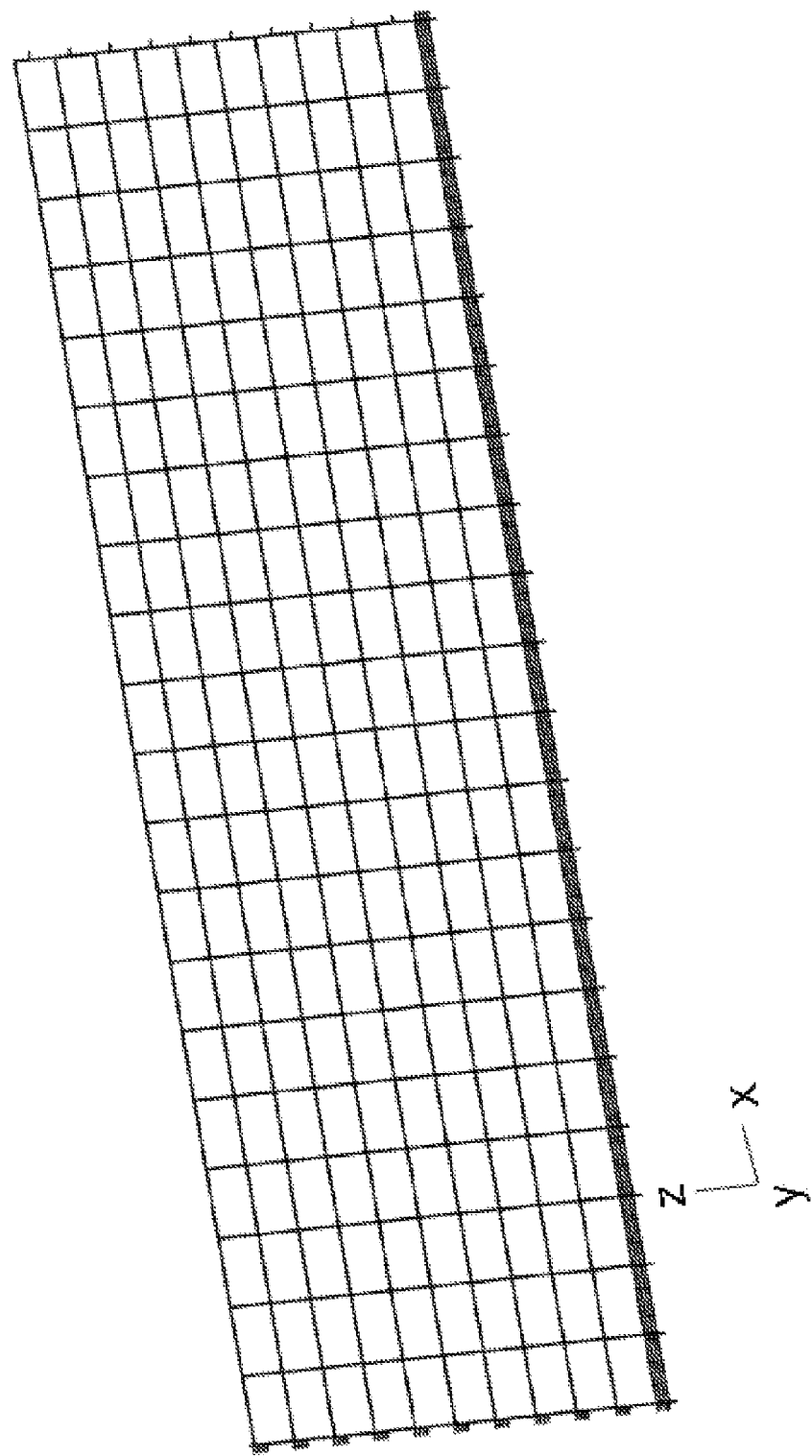
FIG. 15 shows a finite-element-analysis model.
Figure 16:
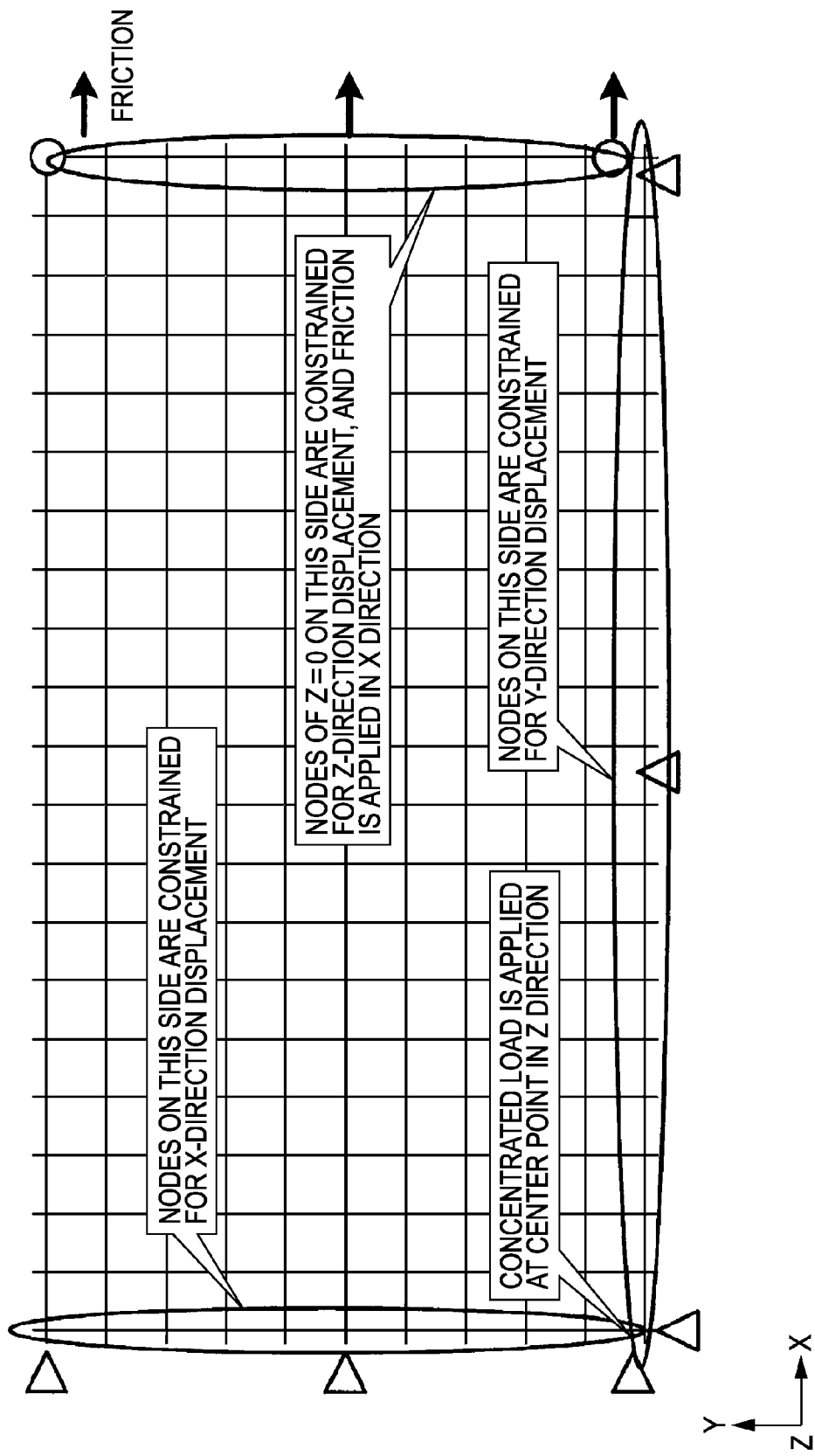
FIG. 16 shows the finite-element-analysis model.

FIGS. 15 and 16 show a finite-element-analysis model. As shown in FIG. 15, after a mesh is generated, a ¼ model is generated taking symmetry into consideration, and constraining and loading conditions, shown in FIG. 16, corresponding to the actual loading conditions are added to the model.

Figure 17:
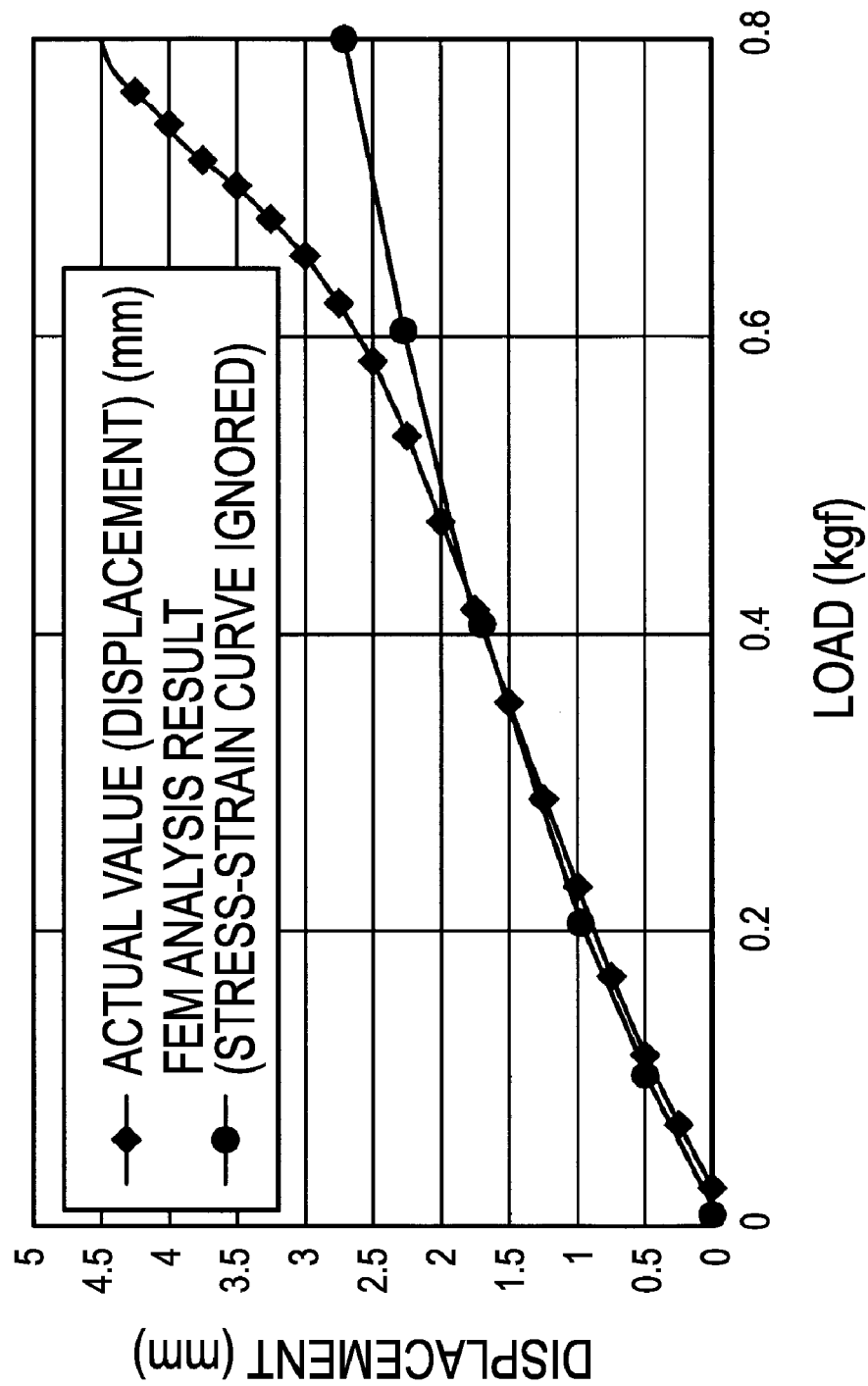
FIG. 17 shows a relationship between FEM analysis results and actual values.

FIG. 17 shows the relationship between the results of an FEM analysis and the actual values. FIG. 18 shows the load-displacement relationship according to the results of the FEM analysis. The relationships shown in FIGS. 17 and 18 are obtained from an FEM analysis in which no stress-strain curve is included and geometric nonlinearity is considered. The analysis results shown in FIGS. 17 and 18 are similar to the solution of a large deformation theory. This analysis was performed with a commercial solver ABAQUS capable of performing nonlinear analysis (a case where a sample analysis file mage4n.inp is input to ABAQUS, with a load of 0.1 kgf). The same analysis can also be performed with any of other kinds of finite element analysis software capable of performing nonlinear analysis.

The parameter-estimating section 150 obtains a provisional stress-strain curve in accordance with the values in case No. 1 shown in FIG. 12, and calculates the warpage (displacement) of the test piece under a specific load from the obtained stress-strain curve by the finite element method.

Figure 19:
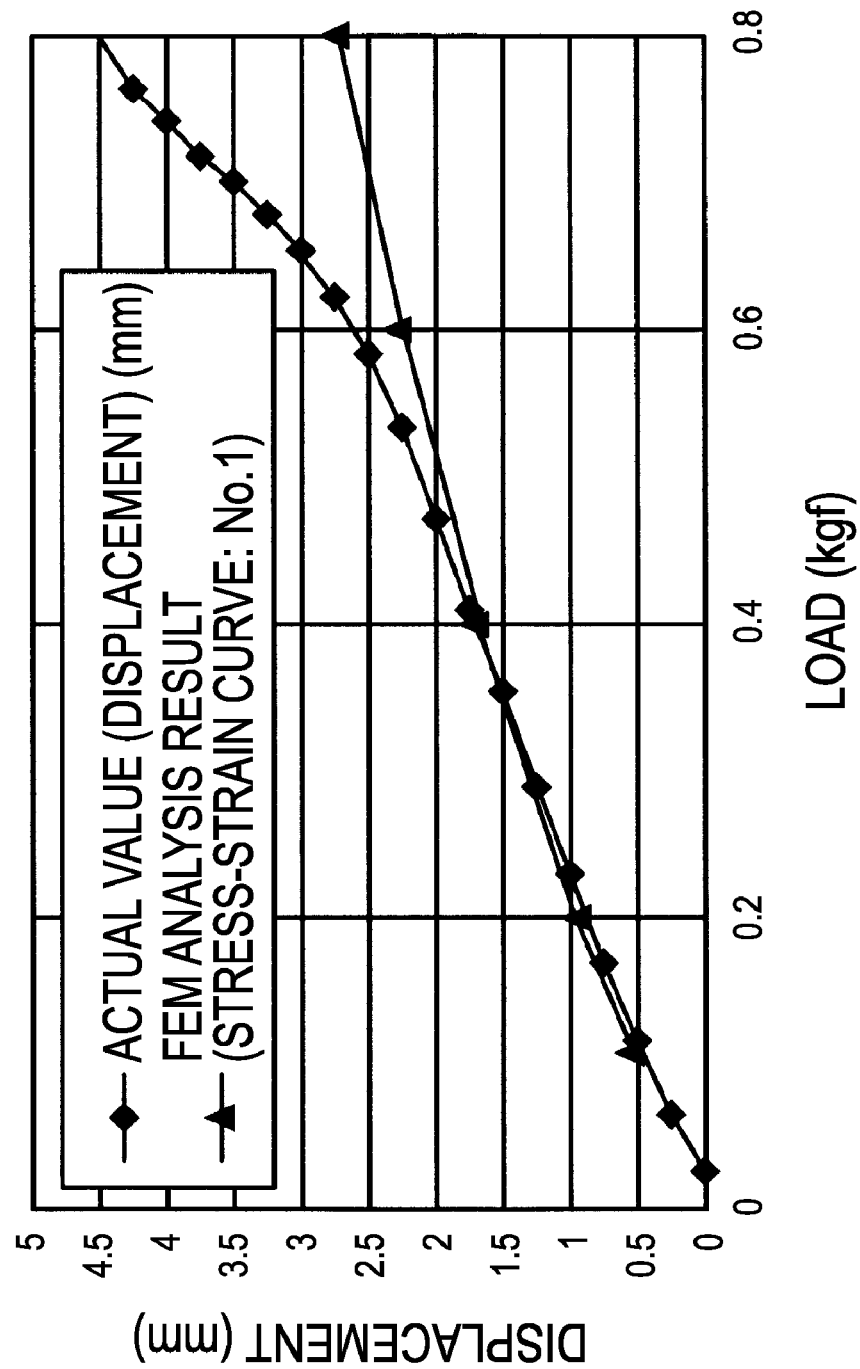
FIG. 19 shows a relationship between the FEM analysis results and the actual values corresponding to case No. 1.

FIG. 19 shows the relationship between the FEM analysis results and the actual values corresponding to case No. 1. FIG. 20 shows the load-displacement relationship according to the FEM analysis results corresponding to case No. 1 (in a case where a sample analysis file mage4n.inp is input to ABAQUS, with a load of 0.1 kgf).

When FIGS. 17 and 19 are compared with each other, no significant difference can be observed, but there are slight differences at the loads 0.6 kgf and 0.8 kgf. The data shown in FIG. 20 includes the relationships between the FEM analysis results and the actual values for the individual loads, and the results of squaring the differences (squared residuals) between the FEM analysis results and the actual values for the individual loads. Referring to FIG. 20, the largest error between the actual value and the FEM analysis result is observed when the load is 0.8 kgf among various loads. The residual sum of squares in case No. 1 is 2.92.

The same as for case No. 1, the parameter-estimating section 150 calculates the residual sum of squares for each of cases No. 2 to No. 9 shown in FIG. 12, and generates a management table that summarizes associations between levels of α, levels of n, and residual sums of squares for individual cases No. 1 to No. 9. FIG. 21 shows an exemplary data structure of the management table.

The parameter-estimating section 150 performs a multiple regression analysis taking the values of α and n shown in FIG. 21 as explaining variables and the residual sums of squares shown in FIG. 21 as an explained variable, thereby expressing the residual sum of squares ρ by the following quadratic approximate expression using α and n:

$$\rho = 2.959 - 0.1136\alpha + 0.624\alpha2 - 0.00301n + 0.000067n2$$

The parameter-estimating section 150 calculates the values of α and n that produce the smallest value of ρ (corresponding to the squared error expressed by Equation (19)) by an optimization algorithm. The results come to α=1 and n=15.

Referring back to FIG. 1, the FEM analysis section 160 is a processing section that calculates, at the acquisition of a virtual stress-strain relationship from the parameter-estimating section 150, the warpage (displacement) of the test piece occurring under a specific load, and outputs the result of the calculation (FEM analysis result) to the parameter-estimating section 150.

Figure 22:
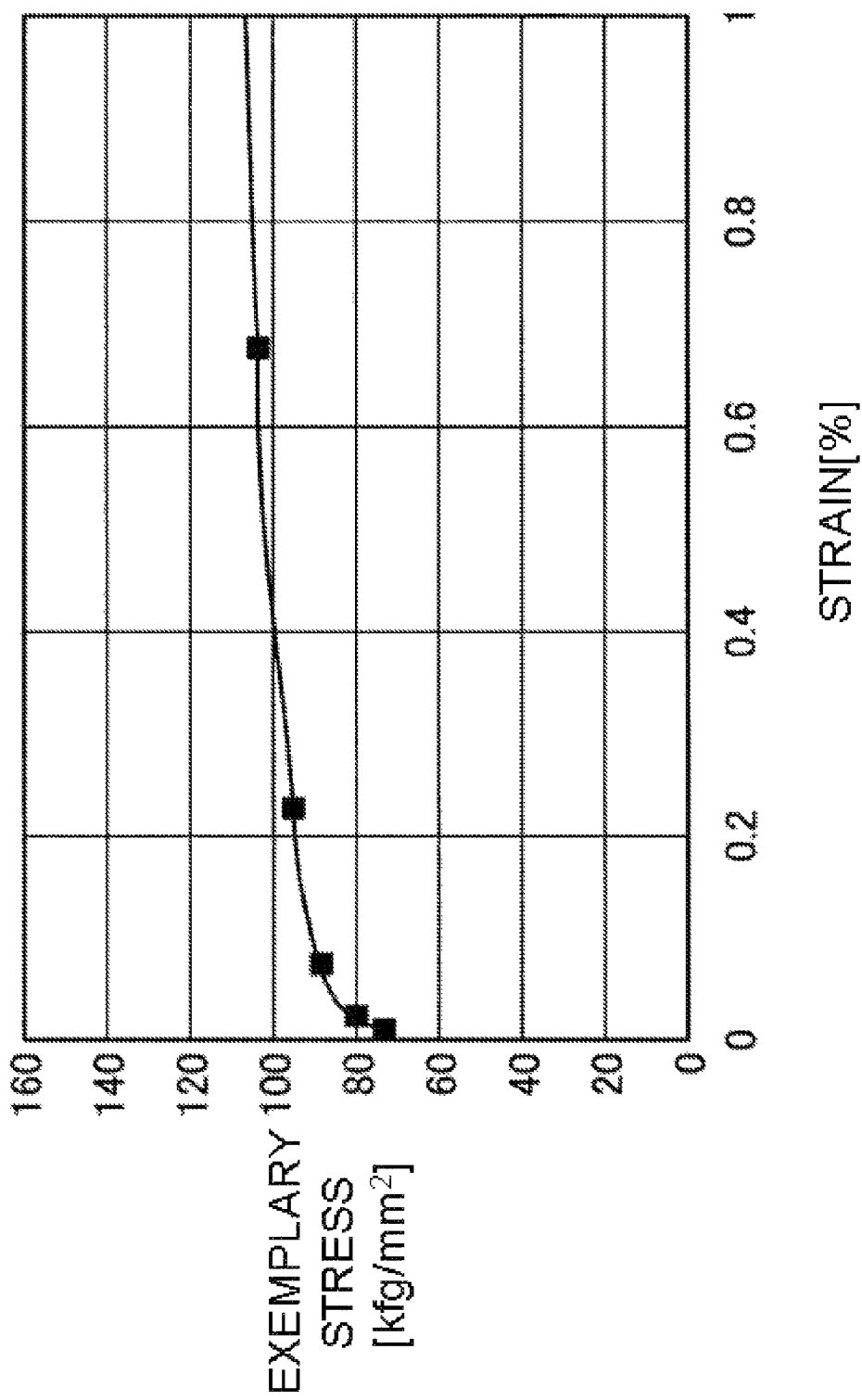
FIG. 22 shows an exemplary stress-strain curve that is output from a stress-strain-curve output section.

The stress-strain-curve output section 170 is a processing section that generates, at the acquisition of an elastic modulus; a yield stress; and parameters α and n, a stress-strain curve in accordance with Equation (18), and outputs the stress-strain curve to an external device such as a printer or a monitor. FIG. 22 shows an exemplary stress-strain curve that is output from the stress-strain-curve output section 170.

Figure 23:
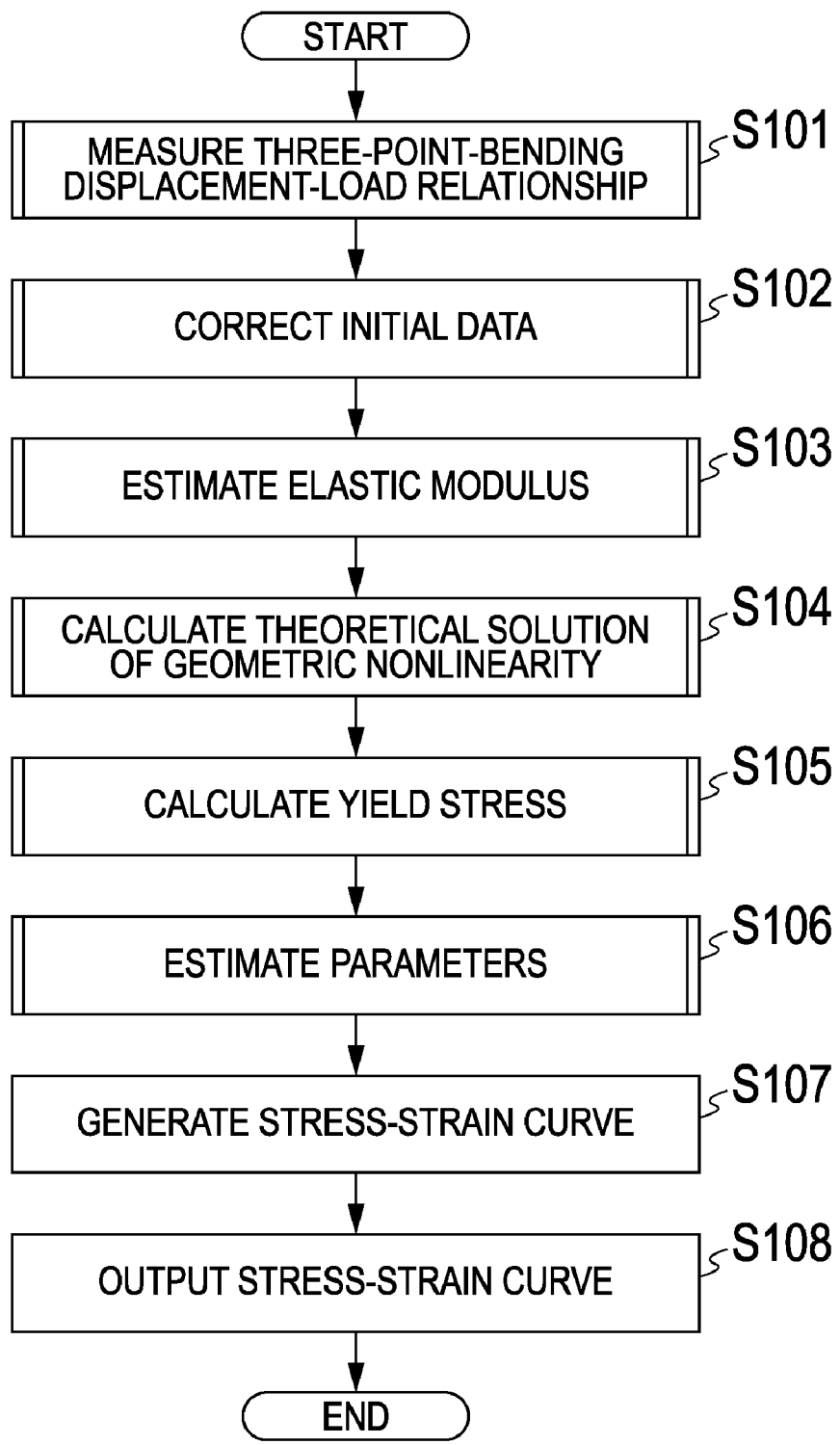
FIG. 23 is a flowchart showing the procedure of operations performed in the measurement apparatus according to the first embodiment.

The procedure of operations performed in the measurement apparatus 100 according to the embodiment 1 will be described. FIG. 23 is a flowchart showing the procedure of operations performed in the measurement apparatus 100 according to the first embodiment. As shown in FIG. 23, the measurement apparatus 100 operates as follows. In step S101, the three-point-bending displacement-load-measuring section 110 measures the displacement-load relationship in a three-point bending test. In step S102, the initial-data-adjusting section 120 corrects initial data.

In step S103, the elastic-modulus-estimating section 130 estimates the elastic modulus. In step S104, the yield-stress-estimating section 140 calculates the theoretical solution of geometric nonlinearity. In step S105, the yield-stress-estimating section 140 calculates the yield stress.

In step S106, the parameter-estimating section 150 estimates the parameters. In step S107, the stress-strain-curve output section 170 generates a stress-strain curve. In step S108, the stress-strain-curve output section 170 outputs the stress-strain curve.

Figure 24:
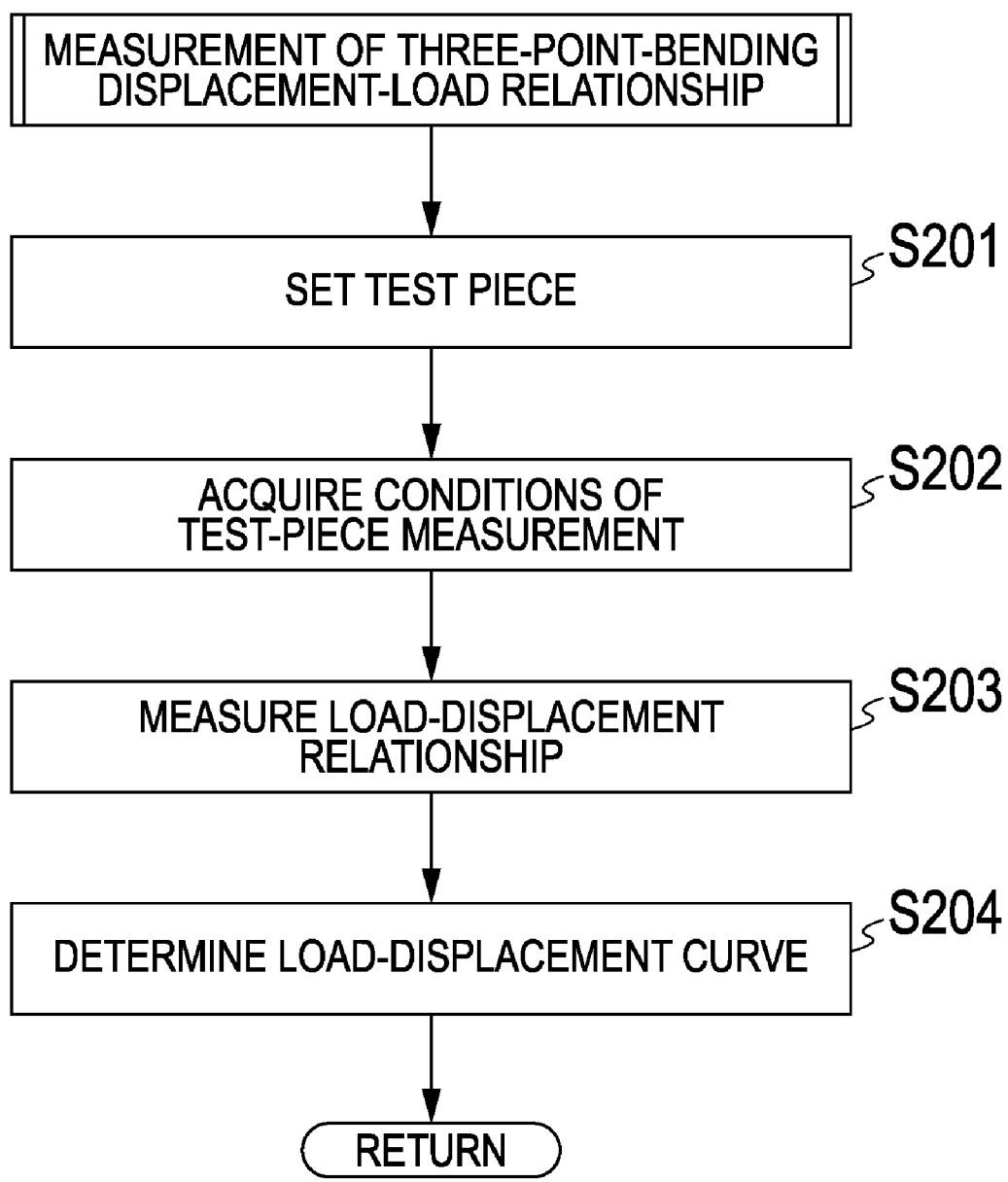
FIG. 24 is a flowchart showing the procedure of measurement of displacement-load relationship in a three-point bending test.

The measurement of displacement-load relationship in a three-point bending test performed in step S101 in FIG. 23 will be described. FIG. 24 is a flowchart showing the procedure of the measurement of displacement-load relationship in a three-point bending test. As shown in FIG. 24, the three-point-bending displacement-load-measuring section 110 performs the following operations. In step S201, a test piece is set. In step S202, conditions of measurement of the test piece are acquired.

In step S203, under the control of a testing device by the three-point-bending displacement-load-measuring section 110, the load-displacement relationship is measured. In step S204, a load-displacement curve is determined.

Figure 25:
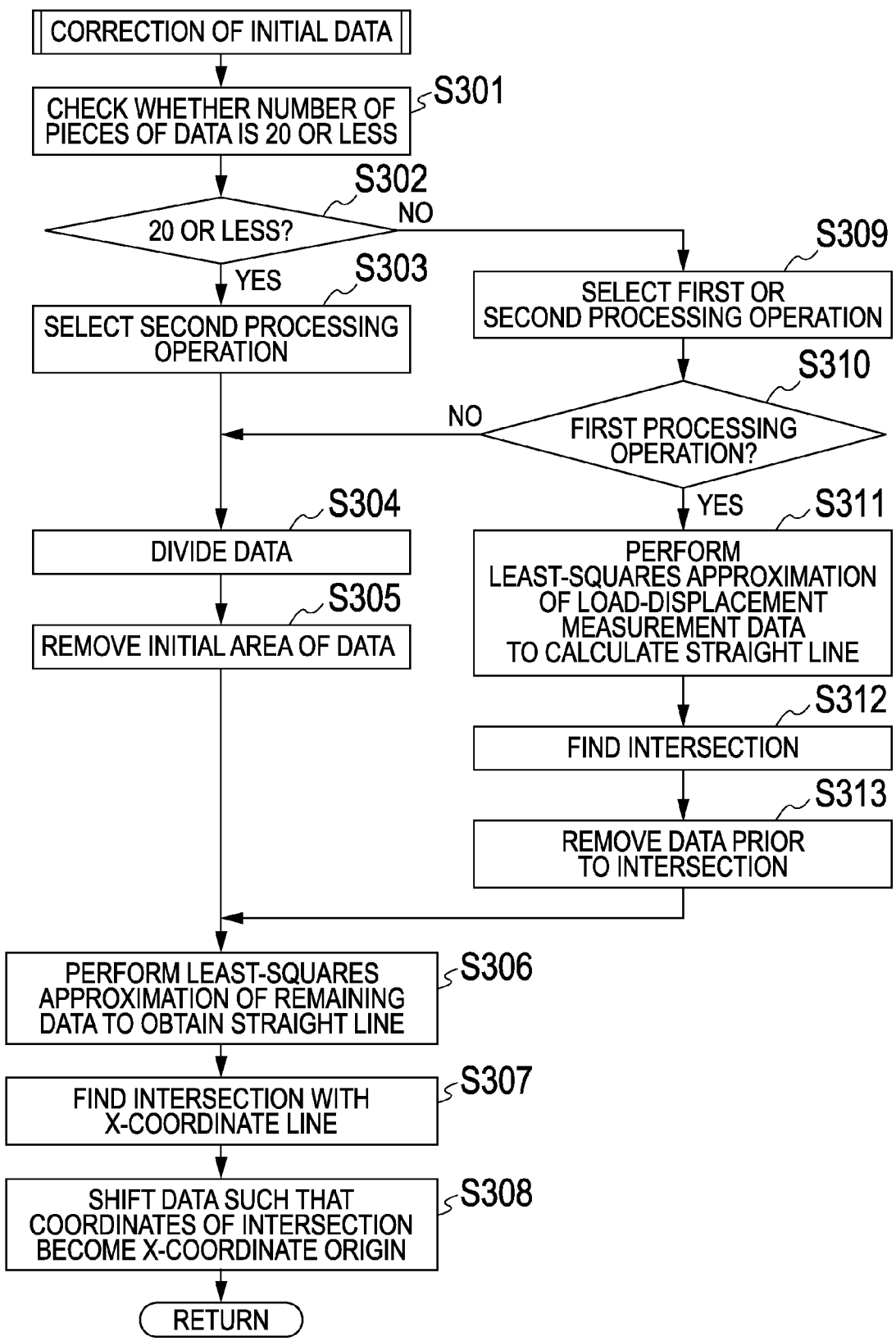
FIG. 25 is a flowchart showing the procedure of initial-data correction.

The correction of initial data performed in step S102 in FIG. 23 will be described. FIG. 25 is a flowchart showing the procedure of the correction of initial data. As shown in FIG. 25, the initial-data-adjusting section 120 performs the following operations. In step S301, load-displacement measurement data is acquired and whether the number of pieces of the data is 20 or less is checked.

In step S302, if the number of pieces of the data is 20 or less (if Yes), the operation proceeds to step S303, in which the second processing operation is selected. In step S304, the load-displacement measurement data is divided into a plurality of areas. In step S305, the initial area of the data is removed.

In step S306, least-squares approximation of the remaining data is performed, whereby a straight line is obtained. In step S307, the point of intersection of the straight line and the X-coordinate line is found. In step S308, the data is shifted such that the coordinates of the point of intersection become the X-coordinate origin.

Whereas, in step S302, if the number of pieces of the load-displacement measurement data is over 20 (if No), the operation proceeds to step S309, in which either of the first and second processing operations is selected. In step S310, if the second processing operation is selected (if No), the operation proceeds to step S304.

In step S310, if the first processing operation is selected (if Yes), the operation proceeds to step S311, in which least-squares approximation of the load-displacement measurement data is performed, whereby a straight line is obtained. In step S312, the point of intersection of the approximate straight line and a curve corresponding to the load-displacement measurement data is found. In step S313, a portion of the data prior to the point of intersection is removed. Then, the operation proceeds to step S306.

Figure 26:
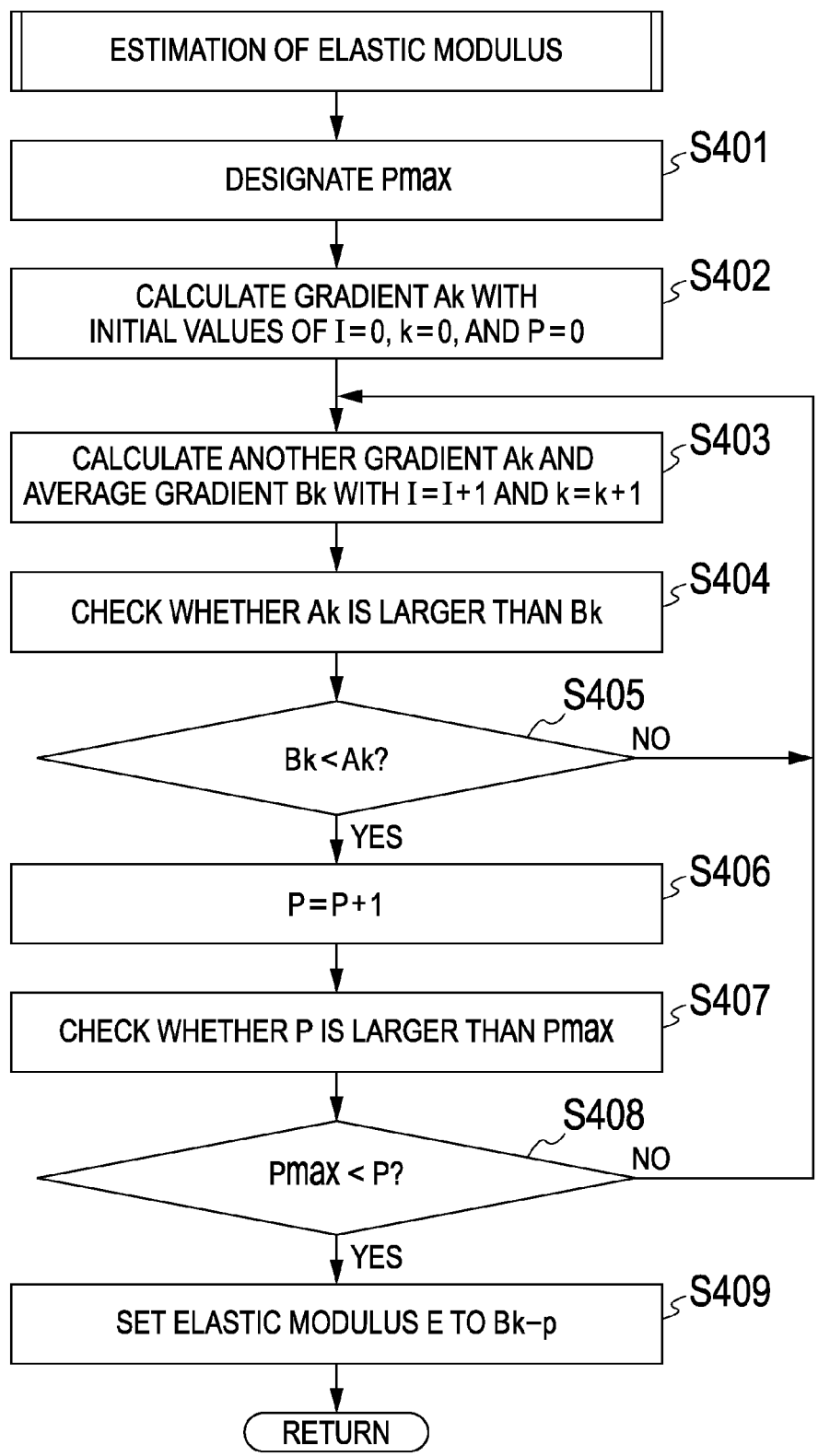
FIG. 26 is a flowchart showing the procedure of elastic modulus estimation.

The estimation of the elastic modulus performed in step S103 in FIG. 23 will be described. FIG. 26 is a flowchart showing the procedure of the elastic modulus estimation. As shown in FIG. 26, the elastic-modulus-estimating section 130 performs the following operations. In step S401, Pmax is designated (or acquired from an administrator). In step S402, a gradient Ak is calculated in accordance with $\Delta u/\Delta F$, with initial values of I=0, k=0, and P=0.

In step S403, another gradient Ak is calculated with values of I=I+1 and k=k+1, and the average gradient Bk is calculated. In step S404, whether or not Ak is larger than Bk is checked. In step S405, if Ak is smaller than or equal to Bk (if No), the operation returns to step S403.

Whereas, in step S404, if Ak is larger than Bk (if Yes), the operation proceeds to step S406, in which P=P+1 is set. In step S407, whether or not P is larger than Pmax is checked. In step S408, if P is not larger than Pmax (if No), the operation returns to step S403. In step S408, if P is larger than Pmax (if Yes), the operation proceeds to step S409, in which the elastic modulus E is set to Bk−p.

Figure 27:
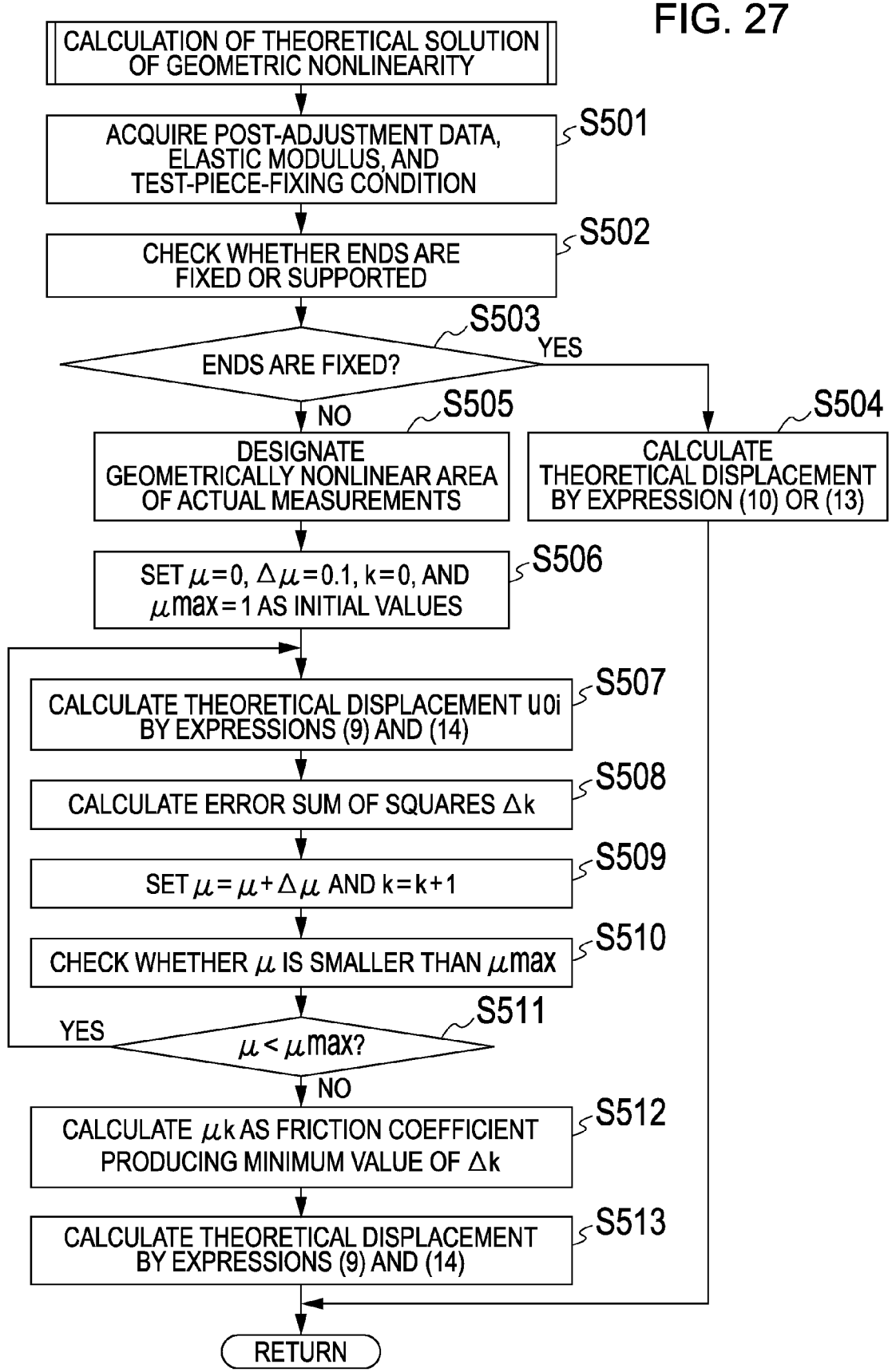
FIG. 27 is a flowchart showing the procedure of calculation of the theoretical solution of geometric nonlinearity.

The calculation of the theoretical solution of geometric nonlinearity performed in step S104 in FIG. 23 will be described. FIG. 27 is a flowchart showing the procedure of the calculation of the theoretical solution of geometric nonlinearity. As shown in FIG. 27, the yield-stress-estimating section 140 performs the following operations. In step S501, the post-adjustment data, the elastic modulus, and a test-piece-fixing condition are acquired. In step S502, whether the test-piece-fixing condition indicates that the ends of the test piece are fixed or supported is checked.

In step S503, if the ends of the test piece are fixed (if Yes), the operation proceeds to step S504, in which the theoretical displacement (warpage) is calculated in accordance with Equation (10) or (13). In step S503, if the ends of the test piece are supported (if No), the operation proceeds to step S505, in which the geometrically nonlinear area of the actual measurement values (post-adjustment data) is designated.

In step S506, $\mu=0$, $\Delta\mu=0.1$, k=0, and $\mu max=1$ are set as initial values. In step S507, the theoretical displacement u0$i$ is calculated in accordance with Equations (9) and (14). In step S508, the error sum of squares Ak is calculated in accordance with $\Sigma(u0i-ui)2 (i=1$ to m).

In step S509, $\mu=\mu+\Delta\mu$ and k=k+1 are set. In step S510, whether or not $\mu$ is smaller than $\mu max$ is checked. In step S511, if $\mu$ is smaller than $\mu max$ (if Yes), the operation returns to step S507.

In step S511, if $\mu$ is not smaller than $\mu max$ (if No), the operation proceeds to step S512, in which $\mu k$ producing the minimum value of $\Delta k$ is calculated as the friction coefficient. In step S513, the theoretical displacement (warpage) is calculated in accordance with Equations (9) and (14).

Figure 28:
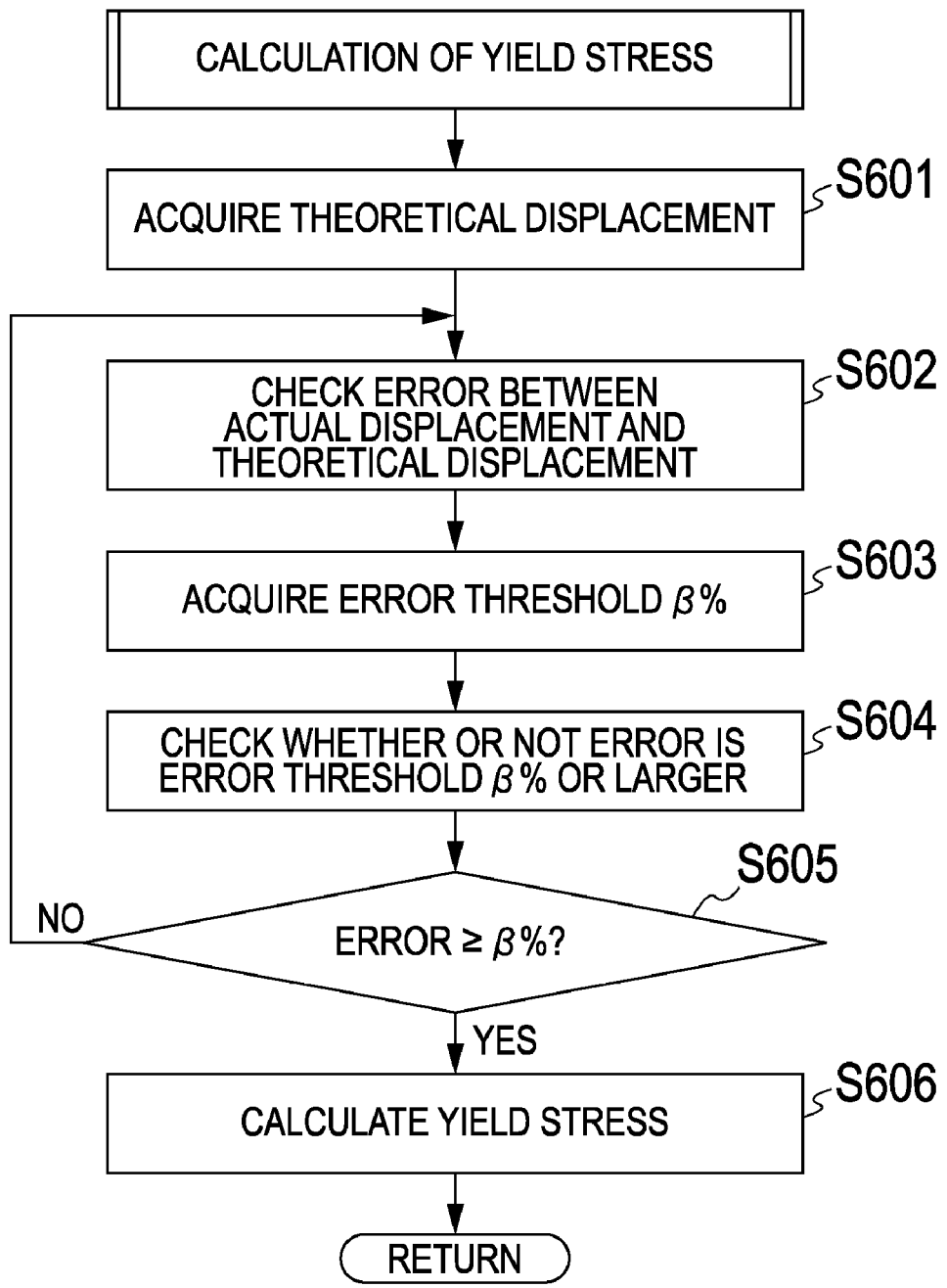
FIG. 28 is a flowchart showing the procedure of yield stress calculation.

The calculation of the yield stress performed in step S105 in FIG. 23 will be described. FIG. 28 is a flowchart showing the procedure of the yield stress calculation. As shown in FIG. 28, the yield-stress-estimating section 140 performs the following operations. In step S601, the theoretical displacement is acquired. In step S602, the error between the actual displacement and the theoretical displacement is checked. In step S601, when the actual displacement is denoted by y0 and the theoretical displacement is denoted by y, the error d is expressed by $100\times(y-y0)/y0$.

In step S603, an error threshold $\epsilon\%$ is acquired. In step S604, whether or not the error is larger than or equal to the error threshold $\beta\%$ is checked. In step S605, if the error is smaller than the error threshold $\beta\%$ (if No), the operation returns to step S602. In step S605, if the error is larger than or equal to the error threshold $\beta\%$ (if Yes), the operation proceeds to step S606, in which the yield stress is calculated.

Figure 29:
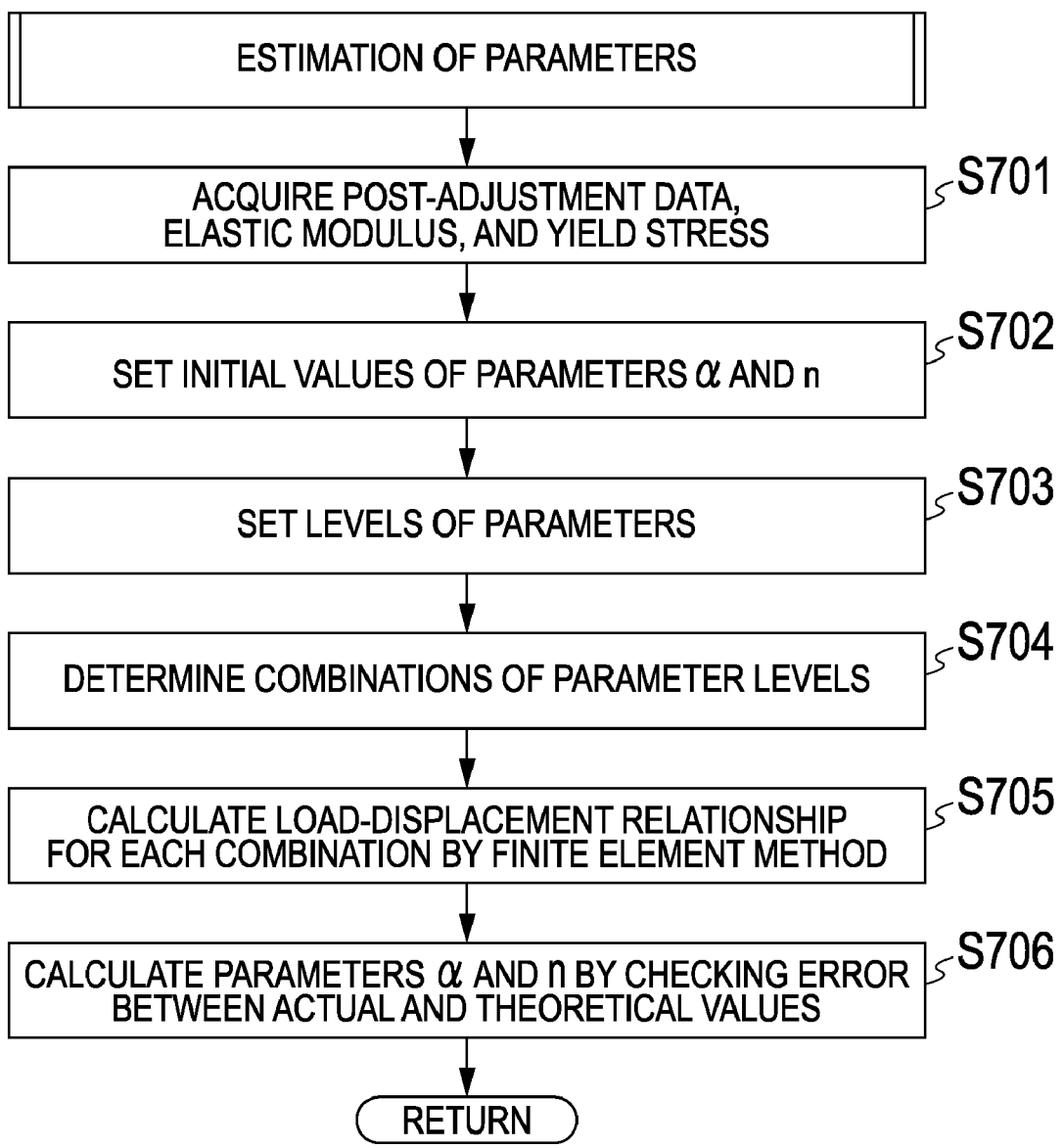
FIG. 29 is a flowchart showing the procedure of parameter estimation.

The estimation of parameters performed in step S106 in FIG. 23 will be described. FIG. 29 is a flowchart showing the procedure of the parameter estimation. As shown in FIG. 29, the parameter-estimating section 150 performs the following operations. In step S701, the post-adjustment data (actual warpage), the elastic modulus, and the yield stress are acquired. In step S702, initial values of the parameters $\alpha$ and n, i.e., the initial material values, are set.

In step S703, levels of the parameters are set. In step S704, combinations of parameter levels are determined. In step S705, the load-displacement relationship is calculated for each of the combinations by a finite element method. In step S706, the errors between the actual values and the theoretical values are checked, whereby the parameters $\alpha$ and n are calculated.

To summarize, the measurement apparatus 100 according to the embodiment 1 operates as follows. After the acquisition of the result of a three-point bending test performed on a test piece, the elastic-modulus-estimating section 130 calculates the elastic modulus of the test piece in accordance with a gradient of a curve representing the load-displacement relationship included in the result of the test. Subsequently, the yield-stress-estimating section 140 calculates the theoretical value representing the relationship between the load to be applied to the test piece and the corresponding displacement for each of different friction coefficients, determines which of the calculated theoretical values produces the smallest error with respect to the result of the test, and calculates the yield stress of the test piece in accordance with the determined theoretical value and the result of the test. Lastly, the parameter-estimating section 150 calculates the stress-strain relationship of the test piece in accordance with the elastic modulus and the yield stress. Thus, the stress-strain characteristic of a material beyond the point of yield stress thereof can be obtained with high accuracy from a displacement-load curve obtained in a three-point bending test.

All or some of the automatically performed processing operations described in the embodiment 1 may alternatively be performed manually. Conversely, all or some of the manually performed processing operations may alternatively be performed automatically by known methods. In addition, information described in this specification and shown in the accompanying drawings, including the operational procedures, control procedures, specific names of elements, and various data and parameters, can arbitrarily be changed unless otherwise specified.

The elements included in the measurement apparatus 100 described in the embodiment 1 are only functional concepts, and the measurement apparatus 100 may not necessarily have the physical configuration shown in the drawings. That is, the distribution and integration of the elements included in the apparatus are not limited to the one shown in the drawings, and all or some of the elements may be functionally or physically distributed and integrated in arbitrary units in accordance with the load and usage that vary with situation. Moreover, all or some of the processing operations performed by the elements described above may be realized by a central processing unit (CPU) and with programs with which analyses are executed by the CPU, or as wired-logic hardware.

Figure 30:
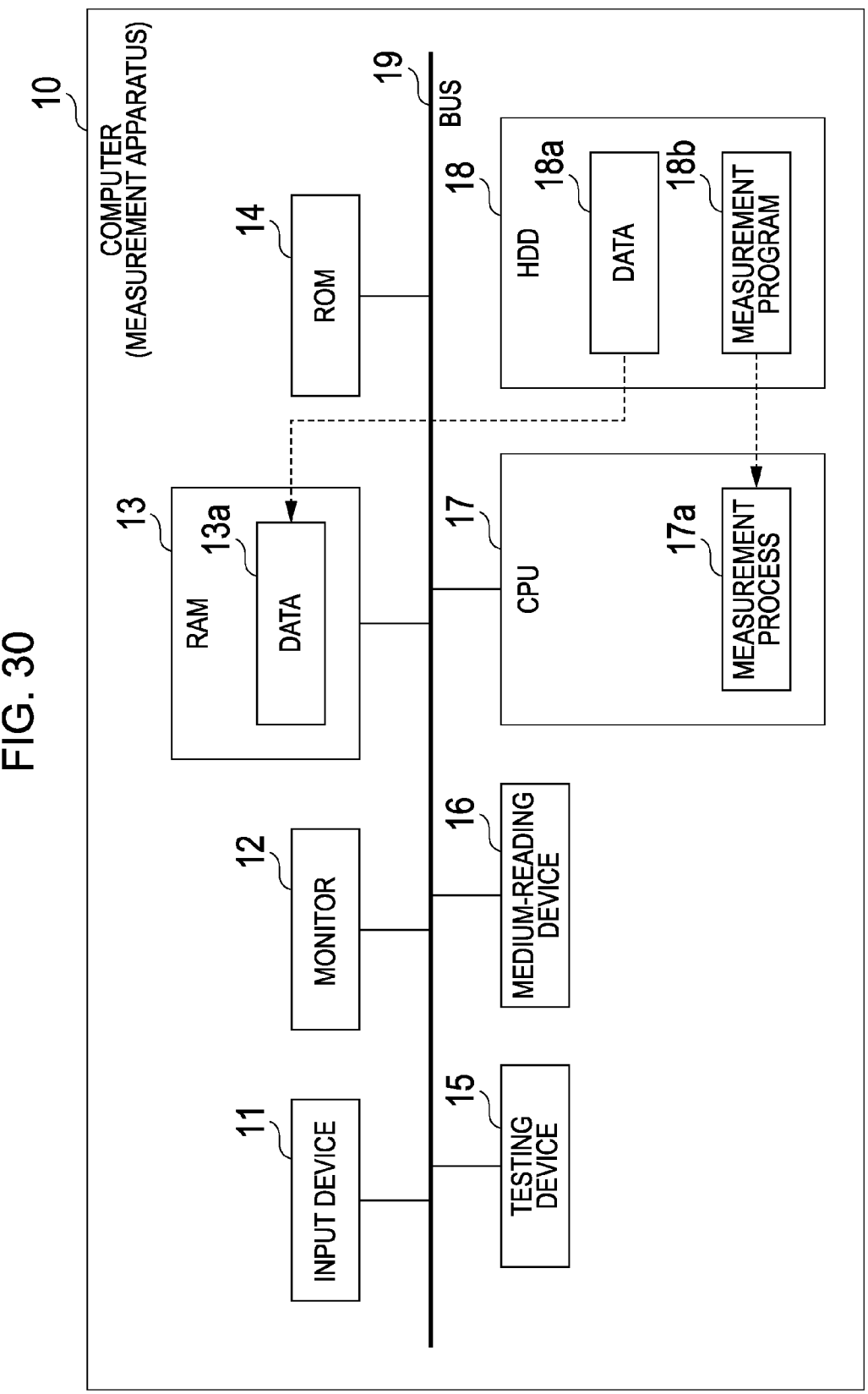
FIG. 30 shows the hardware configuration of a computer corresponding to the measurement apparatus described in the first embodiment.
Figure 31:
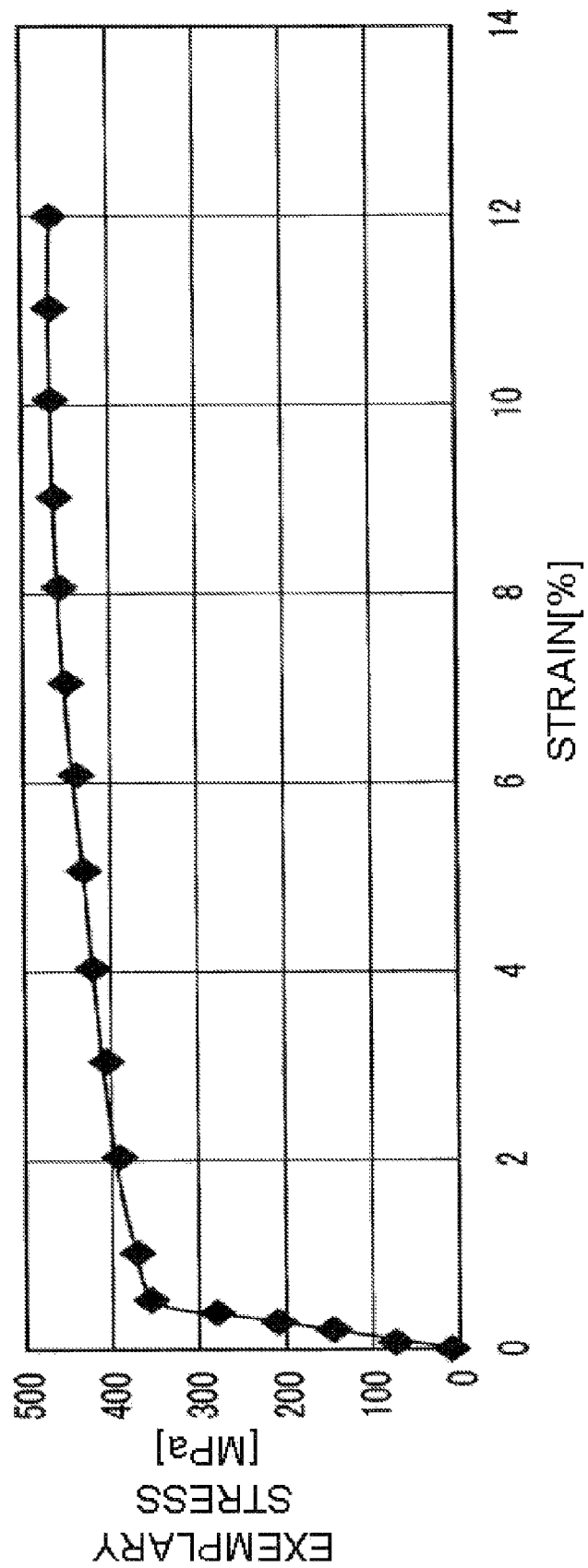
FIG. 31 shows an exemplary stress-strain curve of an aluminum alloy.
Figure 32:
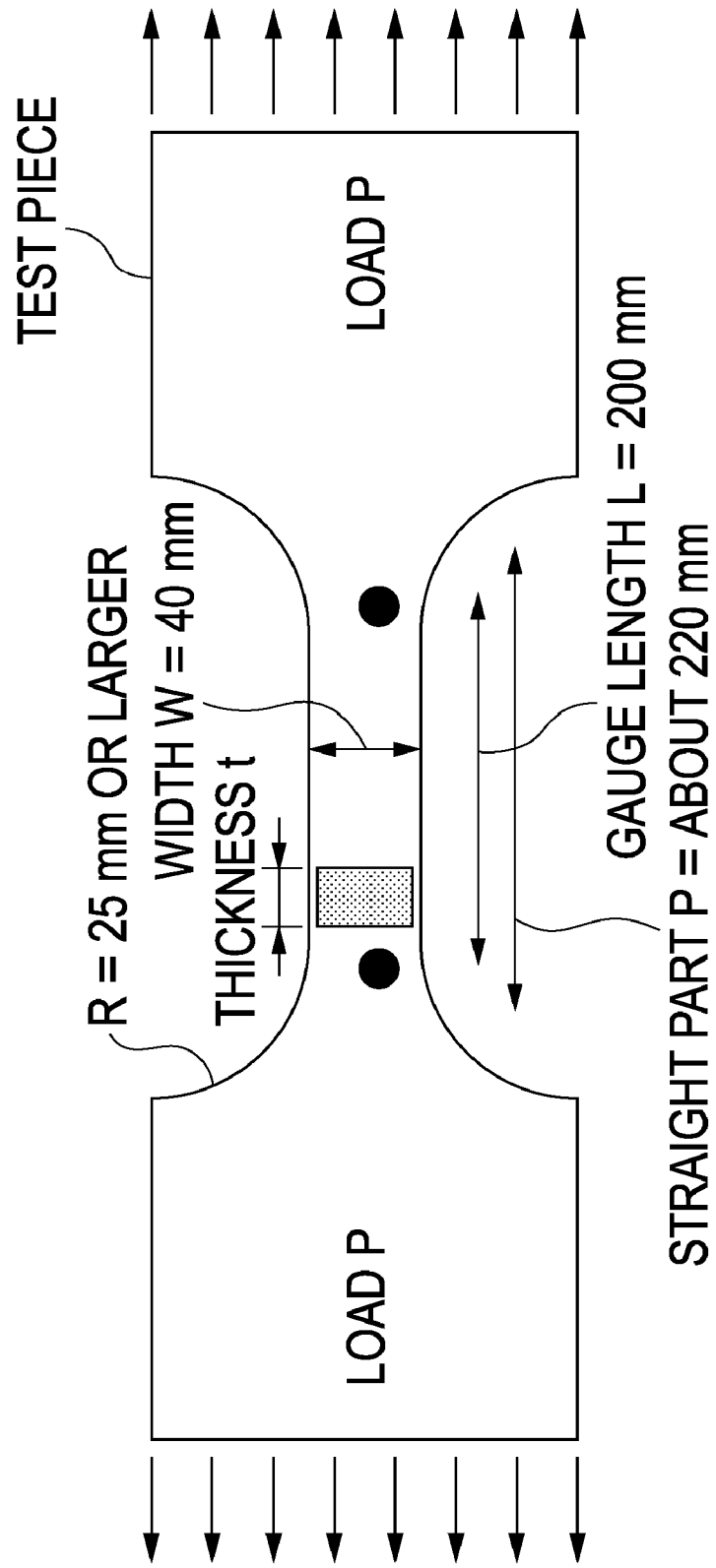
FIG. 32 shows a typical example of No. 1 test piece.

FIG. 30 shows the hardware configuration of a computer corresponding to the measurement apparatus 100 described in the first embodiment. As shown in FIG. 30, a computer (measurement apparatus) 10 includes an input device 11, a monitor 12, a random access memory (RAM) 13, a read-only memory (ROM) 14, a testing device 15 configured to perform a three-point bending test, a medium-reading device 16 configured to read data from a recording medium, a CPU 17, a hard disk drive (HDD) 18, and a bus 19 connecting all the foregoing elements.

The HDD 18 stores a measurement program 18b realizing a function the same as that of the measurement apparatus 100 described in the first embodiment. The CPU 17 reads and executes the measurement program 18b, whereby a measurement process 17a is initiated. The measurement process 17a corresponds to a set of the three-point-bending displacement-load-measuring section 110, the initial-data-adjusting section 120, the elastic-modulus-estimating section 130, the yield-stress-estimating section 140, the parameter-estimating section 150, the FEM analysis section 160, and the stress-strain-curve output section 170 shown in FIG. 1.

The HDD 18 also stores data 18a including the dimensions of a test piece, a test-piece-fixing condition, and so forth. The CPU 17 operates such that the data 18a is read from the HDD 18 into the RAM 13, and the relationship between the stress and the strain acting on the test piece is calculated in accordance with data 13a and the result of the test performed by the testing device 15.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present invention has(have) been described in detail, it should be understood that the various changes, substitutions, and alterations could be made hereto without departing from the spirit and scope of the invention.

What is claimed is:

1. An analyzing apparatus for analyzing strain-stress relation of a test piece by using measurements of the test piece measured by a three-point bending test, the analyzing apparatus comprising:
    an acquisition unit for acquiring data indicative of displacements with respect to loads applied of the test piece measured by the three-point bending test;
    a first calculation unit for calculating a first approximate expression of a relation of the displacements with respect to the loads applied in a first area of a load displacement curve based on the acquired data, where the relation is linear so as to determine an elasticity modulus of the test piece;
    an extraction unit for determining a yield stress value of the test piece by comparing the relation of the displacements with respect to the loads of the test piece with a plurality of reference relations and determining one of the reference relations having a least difference with the relation of the test piece for a friction coefficient of the test piece; and
    a second calculation unit for calculating a second approximate expression of a relation of stress caused by the loads with respect to the strains caused by the displacements in a second area of the load displacement curve beyond the yield stress value on the basis of the yield stress value, the elasticity modulus, and the measurements in the second area of the load displacement curve.

2. The analyzing apparatus according to claim 1, wherein the first calculation unit determines the elasticity modulus on the basis of a slope of a line relating the loads and the displacements.

3. The analyzing apparatus according to claim 1, wherein the extraction unit determines the yield stress value on the basis of the single relation calculated from the size and the friction coefficient of the test piece when both ends of the test piece are fixed.

4. The analyzing apparatus according to claim 1, wherein the second calculation unit executes,
    determining a plurality of relational expressions of the stress and the warp by adjusting a parameter which is included in a calculation expression which is substituting the elasticity modulus and the yield stress into a predetermined model expression,
    calculating a plurality of theoretical values of the relation of the loads and the displacements on the basis of each of the relational expressions, and
    extracting one of the relational expressions as the approximate expression, the relational expression being the expression which corresponds to the theoretical value to which the difference of measurements is minimized.

5. An analyzing method for analyzing strain-stress relation of a test piece by using measurements of the test piece measured by a three-point bending test, the analyzing method comprising:

acquiring data indicative of displacements with respect to loads applied of the test piece measured by the three-point bending test;

calculating, by a processor, a first approximate expression of a relation of the displacements with respect to the loads applied in a first area of a load displacement curve based on the acquired data, where the relation is linear so as to determine an elasticity modulus of the test piece;

determining, by a processor, a yield stress value of the test piece by comparing the relation of the displacements with respect to the loads of the test piece with a plurality of reference relations and determining one of the reference relations having a least difference with the relation of the test piece for a friction coefficient of the test piece; and calculating, by a processor, a second approximate expression of a relation of stress caused by the loads with respect to the strains caused by the displacements in a second area of the load displacement curve beyond the yield stress value on the basis of the yield stress value, the elasticity modulus, and the measurements in the second area of the load displacement curve.

6. The analyzing method according to claim 5 further comprising:

determining the elasticity modulus on the basis of a slope of a line relating the loads and the displacements when calculating the first approximate expression.

7. The analyzing method according to claim 5 further comprising:

determining the yield stress value on the basis of the single relation calculated from the size and the friction coefficient of the test piece when both ends of the test piece are fixed.

8. The analyzing method according to claim 5, further comprising:

determining a plurality of relational expressions of the stress and the warp by adjusting a parameter which is included in a calculation expression which is substituting the elasticity modulus and the yield stress into a predetermined model expression;

calculating a plurality of theoretical values of the relation of the loads and the displacements on the basis of each of the relational expressions; and extracting one of the relational expressions as the approximate expression, the relational expression being the expression which corresponds to the theoretical value to which the difference of measurements is minimized.

9. A non-transitory computer-readable recording medium storing a analyzing program containing instructions executable on a computer, the program causing the computer to execute:

acquiring data indicative of displacements with respect to loads applied of the test piece measured by the three-point bending test;

calculating a first approximate expression of a relation of the displacements with respect to the loads applied in a first area of a load displacement curve based on the acquired data, where the relation is linear so as to determine an elasticity modulus of the test piece;

determining a yield stress value of the test piece by comparing the relation of the displacements with respect to the loads of the test piece with a plurality of reference relations and determining one of the reference relations having a least difference with the relation of the test piece for a friction coefficient of the test piece; and calculating a second approximate expression of a relation of stress caused by the loads with respect to the strains caused by the displacements in a second area of the load displacement curve beyond the yield stress value on the basis of the yield stress value, the elasticity modulus, and the measurements in the second area of the load displacement curve.

* * * * *